(12) United States Patent
Wagner et al.

(10) Patent No.: US 10,149,750 B2
(45) Date of Patent: Dec. 11, 2018

(54) GRAFT DEVICES AND METHODS OF FABRICATION

(71) Applicant: Neograft Technologies, Inc., Taunton, MA (US)

(72) Inventors: David Wagner, East Greenwich, RI (US); Lorenzo Soletti, Pittsburgh, PA (US); Mohammed S. El-Kurdi, Mansfield, MA (US); Jon McGrath, Duxbury, MA (US); John T. Garibotto, Marblehead, MA (US); J. Christopher Flaherty, Topsfield, MA (US)

(73) Assignee: NEOGRAFT TECHNOLOGIES, INC., Taunton, MA (US)

( * ) Notice: Subject to any disclaimer, the term of this patent is extended or adjusted under 35 U.S.C. 154(b) by 117 days.

(21) Appl. No.: 15/044,369

(22) Filed: Feb. 16, 2016

(65) Prior Publication Data

US 2016/0157989 A1 Jun. 9, 2016

Related U.S. Application Data

(63) Continuation of application No. 13/520,009, filed as application No. PCT/US2010/062487 on Dec. 30, 2010, now Pat. No. 9,295,541.

(Continued)

(51) Int. Cl.
*A61F 2/06* (2013.01)
*A61L 27/18* (2006.01)
(Continued)

(52) U.S. Cl.
CPC ............ *A61F 2/06* (2013.01); *A61F 2/064* (2013.01); *A61L 27/047* (2013.01); *A61L 27/14* (2013.01);
(Continued)

(58) Field of Classification Search
CPC .... A61F 2/04; A61F 2250/0039; A61F 2/064; A61F 2210/0076; A61F 2/06;
(Continued)

(56) References Cited

U.S. PATENT DOCUMENTS 4,323,525 A * 4/1982 Bornat .................... A61F 2/06
264/441
4,441,215 A 4/1984 Kaster
(Continued)

FOREIGN PATENT DOCUMENTS

CA 2677033 A1 8/2008
CN 1491728 A 4/2004
(Continued)

OTHER PUBLICATIONS

Alcocer, et al. Mutual exclusion of apoptosis and hsp70 in human vein intimal hyperplasia in vitro. J Surg Res. 2001;96(1): 75-80.
(Continued)

*Primary Examiner* — Christine H Matthews
*Assistant Examiner* — Joshua D Lannu
(74) *Attorney, Agent, or Firm* — Wilson Sonsini Goodrich & Rosati

(57) ABSTRACT

A graft device is provided comprising a flow conduit and a surrounding covering. The graft device can connect a first body space and a second body space. In one embodiment, the flow conduit is a vein, such as a harvested saphenous vein, useful as an arterial graft, for example and without limitation, in a coronary artery bypass procedure. Also provided are methods of preparing a graft device and connecting the graft device between a first body space and a second body space, such as the aorta and a location on an occluded coronary artery, distal to the occlusion.

28 Claims, 16 Drawing Sheets

CURVILINEAR GRAFT

Related U.S. Application Data

(60) Provisional application No. 61/291,820, filed on Dec. 31, 2009.

(51) Int. Cl.
*A61L 27/56* (2006.01)
*A61L 27/58* (2006.01)
*A61L 27/54* (2006.01)
*A61L 27/04* (2006.01)
*A61L 27/16* (2006.01)
*A61L 27/34* (2006.01)
*A61L 27/14* (2006.01)
*A61L 27/36* (2006.01)
*A61F 2/04* (2013.01)

(52) U.S. Cl.
CPC .............. *A61L 27/16* (2013.01); *A61L 27/18* (2013.01); *A61L 27/34* (2013.01); *A61L 27/36* (2013.01); *A61L 27/54* (2013.01); *A61L 27/56* (2013.01); *A61L 27/58* (2013.01); *A61F 2/04* (2013.01); *A61F 2210/0076* (2013.01); *A61F 2250/0039* (2013.01); *A61L 2300/412* (2013.01); *A61L 2430/36* (2013.01)

(58) Field of Classification Search
CPC .......... A61L 27/14; A61L 27/36; A61L 27/58; A61L 2430/36; A61L 27/34; A61L 27/18; A61L 27/16; A61L 27/047; A61L 27/56; A61L 27/54; A61L 2300/412
See application file for complete search history.

(56) References Cited

U.S. PATENT DOCUMENTS

| | | |
|---|---|---|
| 4,552,707 A | 11/1985 | How |
| 4,689,186 A | 8/1987 | Bornat |
| 4,738,740 A | 4/1988 | Pinchuk |
| 4,798,606 A | 1/1989 | Pinchuk |
| 4,955,899 A | 9/1990 | Della Corma et al. |
| 5,024,789 A | 6/1991 | Berry |
| 5,662,700 A | 9/1997 | Lazarus |
| 5,813,167 A | 9/1998 | Hoshino et al. |
| 6,030,371 A | 2/2000 | Pursley |
| 6,036,702 A | 3/2000 | Bachinski et al. |
| 6,036,724 A | 3/2000 | Lentz et al. |
| 6,165,212 A | 12/2000 | Dereume et al. |
| 6,187,038 B1 | 2/2001 | Sullivan et al. |
| 6,237,567 B1* | 5/2001 | Nakano ................ F02D 41/008 123/446 |
| 6,296,863 B1 | 10/2001 | Trogolo et al. |
| 6,440,163 B1 | 8/2002 | Swanson et al. |
| 6,572,650 B1 | 6/2003 | Abraham et al. |
| 6,599,323 B2 | 7/2003 | Melican et al. |
| 6,891,077 B2 | 5/2005 | Rothwell et al. |
| 7,033,388 B2 | 4/2006 | Zilla et al. |
| 7,037,332 B2 | 5/2006 | Kutryk et al. |
| 7,150,742 B2* | 12/2006 | Takamoto ............... A61B 17/11 128/899 |
| 7,166,124 B2 | 1/2007 | Xie et al. |
| 7,192,440 B2 | 3/2007 | Anreas et al. |
| 7,326,237 B2 | 2/2008 | Depalma et al. |
| 7,374,774 B2 | 5/2008 | Bowlin et al. |
| 7,413,575 B2 | 8/2008 | Phaneuf et al. |
| 7,452,374 B2 | 11/2008 | Hain et al. |
| 7,531,503 B2 | 5/2009 | Atala et al. |
| 7,641,844 B2 | 1/2010 | Melsheimer |
| 7,759,099 B2 | 7/2010 | Wolf et al. |
| 7,759,120 B2 | 7/2010 | Wolf et al. |
| 7,794,219 B2 | 9/2010 | Dubson et al. |
| 7,833,267 B2 | 11/2010 | Flagle et al. |
| 7,901,446 B2 | 3/2011 | Flagle et al. |
| 7,905,826 B2 | 3/2011 | Case et al. |
| 7,922,761 B2 | 4/2011 | Shalev et al. |
| 7,998,188 B2 | 8/2011 | Zilla et al. |
| 8,057,537 B2 | 11/2011 | Zilla et al. |
| 8,076,529 B2 | 12/2011 | Ehrenreich et al. |
| 8,172,746 B2 | 5/2012 | Zilla et al. |
| 8,267,989 B2 | 9/2012 | Whirley et al. |
| 8,292,799 B2 | 10/2012 | Xu |
| 8,353,814 B2 | 1/2013 | Villafana et al. |
| 8,491,457 B2 | 7/2013 | Atala et al. |
| 9,295,541 B2 | 3/2016 | Wagner et al. |
| 2002/0004663 A1 | 1/2002 | Gittings et al. |
| 2002/0022853 A1 | 2/2002 | Swanson et al. |
| 2002/0042128 A1 | 4/2002 | Bowlin et al. |
| 2002/0123786 A1 | 9/2002 | Gittings et al. |
| 2003/0109887 A1 | 6/2003 | Galdonik et al. |
| 2004/0054406 A1 | 3/2004 | Dubson et al. |
| 2004/0073294 A1 | 4/2004 | Diaz et al. |
| 2004/0094873 A1 | 5/2004 | Dubson et al. |
| 2004/0146546 A1 | 7/2004 | Gravett et al. |
| 2004/0171545 A1 | 9/2004 | Chaikof et al. |
| 2004/0219185 A1 | 11/2004 | Ringeisen |
| 2005/0182484 A1 | 8/2005 | Patel |
| 2005/0203636 A1 | 9/2005 | McFetridge |
| 2006/0085063 A1 | 4/2006 | Shastri et al. |
| 2006/0240061 A1* | 10/2006 | Atala ..................... A61F 2/06 424/422 |
| 2006/0257447 A1 | 11/2006 | Hinds et al. |
| 2007/0087027 A1 | 1/2007 | Greenhalgh et al. |
| 2007/0173917 A1 | 7/2007 | Hayashi et al. |
| 2007/0213838 A1 | 9/2007 | Hengelmolen |
| 2007/0239267 A1 | 10/2007 | Hendriks et al. |
| 2007/0265643 A1 | 11/2007 | Beane et al. |
| 2007/0269481 A1 | 11/2007 | Li et al. |
| 2008/0082161 A1 | 4/2008 | Woo |
| 2008/0208323 A1 | 8/2008 | El-Kurdi et al. |
| 2009/0012607 A1 | 1/2009 | Kim et al. |
| 2009/0030580 A1 | 1/2009 | Tang et al. |
| 2009/0088828 A1 | 4/2009 | Shalev et al. |
| 2010/0160718 A1 | 6/2010 | Villafana et al. |
| 2010/0233115 A1 | 9/2010 | Patel et al. |
| 2010/0280598 A1 | 11/2010 | Fox |
| 2010/0331964 A1 | 12/2010 | Clerin et al. |
| 2011/0288628 A1 | 11/2011 | Noesner et al. |
| 2012/0116495 A1 | 5/2012 | Zilla et al. |
| 2012/0296353 A1 | 11/2012 | Wagner et al. |

FOREIGN PATENT DOCUMENTS

| | | |
|---|---|---|
| EP | 0095940 A2 | 12/1983 |
| EP | 0265176 A2 | 4/1988 |
| JP | H 1176278 A | 3/1999 |
| JP | 2003235880 A | 8/2003 |
| JP | 2004525272 A | 8/2004 |
| JP | 2006515186 A | 5/2006 |
| JP | 2006526658 A | 11/2006 |
| KR | 100595487 B1 | 7/2006 |
| WO | WO 98/32367 A2 | 7/1998 |
| WO | WO-0226310 A1 | 4/2002 |
| WO | WO 2004/028583 A2 | 4/2004 |
| WO | WO 2006/044904 A2 | 4/2006 |
| WO | WO 2007/003199 A1 | 1/2007 |
| WO | WO 2009/103012 A1 | 8/2009 |
| WO | WO 2010/042721 A1 | 4/2010 |
| WO | WO 2011/056705 A2 | 5/2011 |
| WO | WO 2011/082295 A2 | 7/2011 |
| WO | WO 2011/084559 A2 | 7/2011 |

OTHER PUBLICATIONS

Angelini, et al. Distention promotes platelet and leukocyte adhesion and reduces short-term patency in pig arteriovenous bypass grafts. J Thorac Cardiovasc Surg. 1990;99(3): 4339.

Annabi, et al. Differential regulation of matrix metalloproteinase activities in abdominal aortic aneurysms. J Vasc Surg. 2002;35(3): 539-46.

Asanuma, et al. Uniaxial strain upregulates matrix-degrading enzymes produced by human vascular smooth muscle cells. Am J Physiol Heart Circ Physiol. 2003;284(5): H1778-84.

(56) References Cited

OTHER PUBLICATIONS

Ayres, et al. Modulation of anisotropy in electrospun tissue-engineering scaffolds: Analysis of fiber alignment by the fast Fourier transform. Biomaterials 27 (2006) 5524-5534.
Bandyk, et al. The failing graft: An evolving concept. Semin Vasc Surg. 1993;6(2): 75-7.
Bassiouny, et al. Anastomotic intimal hyperplasia: Mechanical injury or flow induced. J Vasc Surg. 1992;15(4): 708-16; discussion 716-7.
Bassiouny, et al. Low flow enhances platelet activation after acute experimental arterial injury. J Vasc Surg. 1998;27(5): 910-8.
Ben-Gal, et al. Expandable external support device to improve saphenous vein graft patency after cabg. J Cardiothorac Surg 2013;8:122.
Berkowitz, et al. Reversed vein graft stenosis: Early diagnosis and management. J Vasc Surg. 1992;15(1): 130-41; discussion 141-2.
Bornstein, P. Diversity of function is inherent in matricellular proteins: An appraisal of thrombospondin 1. J Cell Biol. 1995;130(3): 503-6.
Brant, et al. Measurement in vitro of pulsatile arterial diameter using a helium-neon laser. J Appl Physiol. 1987;62(2): 679-83.
Bunt, TJ. Synthetic vascular graft infections. I. Graft infections. Surgery. 1983;93(6): 733-46.
Cabrera-Fischer, et al. Reduced elastic mismatch achieved by interposing vein cuff in expanded polytetrafluoroethylene femoral bypass decreases intimal hyperplasia. Artif Organs. 2005;29(2): 122-30.
Cagiannos, et al. Rapamycin-coated expanded polytetrafluoroethylene bypass grafts exhibit decreased anastomotic neointimal hyperplasia in a porcine model. J Vasc Surg. 2005;42(5): 980-8.
Campbell, et al. Arterial smooth muscle. A multifunctional mesenchymal cell. Arch Pathol Lab Med. 1988;112(10): 977-86.
Campbell, et al. Vein grafts for arterial repair: Their success and reasons for failure. Ann R Coll Surg Engl. 1981;63(4): 257-60.
Chakrabarty, S. Fibrin solubilizing properties of certain anionic and cationic detergents. Thrombosis research 55.4 (1989): 511-519.
Cho, et al. Matrix metalloproteinase-9 is necessary for the regulation of smooth muscle cell replication and migration after arterial injury. Circ Res. 2002;91(9): 845-51.
Courtney, et al. Design and analysis of tissue engineering scaffolds that mimic soft tissue mechanical anisotropy. Biomaterials. 2006, 27: 3631-3638.
Davies, et al. Pre-bypass morphological changes in vein grafts. Eur J Vasc Surg. 1993;7(6): 642-7.
Davies, et al. Prevention of malalignment during non-reversed femorodistal bypass. Ann R Coll Surg Engl. 1992;74(6): 434-5.
Deitzel, et al. Controlled deposition of electrospun poly(ethylene oxide) fibers. Polymer. 2001, 42: 8163-8170.
Deitzel, et al. The effect of processing variable on the morphology of electrospun nanofibers and textiles. Polymer 42 (2001): 261-272.
Dethlefsen, et al. Comparison of the effects of mechanical stimulation on venous and arterial smooth muscle cells in vitro. J Vasc Res. 1996;33(5): 40513.
Dobrin, et al. Mechanical factors predisposing to intimal hyperplasia and medial thickening in autogenous vein grafts. Surgery. 1989;105(3): 393-400.
Ducasse, et al. Interposition vein cuff and intimal hyperplasia: An experimental study. Eur J Vasc Endovasc Surg. 2004;27(6): 617-21.
Edwards, et al. Primary graft infections. J Vasc Surg. 1987;6(3): 235-9.
Francis, et al. Release of platelet-derived growth factor activity from pig venous arterial grafts. J Thorac Cardiovasc Surg. 1994;108(3): 540-8.
Fuchs, et al. Postoperative changes in autologous vein grafts. Ann Surg. 1978;188(1): 1-15.
Fujimoto, et al. An elastic, biodegradable cardiac patch induces contractile smooth muscle and improves cardiac remodeling and function in subacute myocardial infarction. J Am Coll Cardiol. 2007;49(23): 2292-300.
Fujimoto, et al. In vivo evaluation of a porous, elastic, biodegradable patch for reconstructive cardiac procedures. Ann Thorac Surg. 2007;83(2): 648-54.
Galis, et al. Cytokine-stimulated human vascular smooth muscle cells synthesize a.complement of enzymes required for extracellular matrix digestion. Circulation Research (Online). 1994;75(1): 181-9.
Garanich, et al. Shear stress inhibits smooth muscle cell migration via nitric oxide-mediated downregulation of matrix metalloproteinase-2 activity. Am J Physiol Heart Circ Physiol. 2005;288(5): H2244-52.
George, et al. Adenovirus-mediated gene transfer of the human TIMP-1 gene inhibits smooth muscle cell migration and neointimal formation in human saphenous vein. Hum Gene Then 1998;9(6): 867-77.
George, et al. Gene transfer of tissue inhibitor of metalloproteinase-2 inhibits metalloproteinase activity and neointima formation in human saphenous veins. Gene Ther. 1998;5(11): 1552-60.
George, et al. Surgical preparative injury and neointima formation increase MMP-9 expression and MMP-2 activation in human saphenous vein. Cardiovasc Res. 1997;33(2): 447-59.
Goldman, et al. Degradation of alpha-actin filaments in venous smooth muscle cells in response to mechanical stretch. Am J Physiol Heart Circ Physiol. 2003;284(5): H1839-47.
Goldman, et al. Negative regulation of vascular smooth muscle cell migration by blood shear stress. Am J Physiol Heart Circ Physiol. 2007;292(2): H928-38.
Greenwood, et al. Restructuring of focal adhesion plaques by pi 3-kinase. Regulation by ptdins (3,4,5)-p(3) binding to alpha-actinin. J Cell Biol. 2000;150(3): 627-42.
Grote, et al. Mechanical stretch enhances mRNA expression and proenzyme release of matrix metalloproteinase-2 (MMP-2) via nad(p)h oxidase-derived reactive oxygen species. Circulation Research. 2003;92(11): 80-6.
Guan, et al. Synthesis, characterization, and cytocompatibility of elastomeric, biodegradable poly(ester-urethane)ureas based on poly(caprolactone) and putrescine. J Biomed Mater Res. 2002;61(3): 493-503.
Gusic, et al. Shear stress and pressure modulate saphenous vein remodeling ex vivo. J Biomech. 2005;38(9): 1760-9.
Hayashi, K. Experimental approaches on measuring the mechanical properties and constitutive laws of arterial walls. J Biomech Eng. 1993;115(4B): 481-8.
He et al., Arterial Replacement with Compliant Hierarchic Hybrid Vascular Graft: Biomechanical Adaptation and Failure Tissue Engineering, 2002, pp. 213-224, 8(2).
Hermans, et al. Fibrin: structure and interactions. Seminars in thrombosis and hemostasis. vol. 8. No. 1. 1982.
Hilker, et al. Bypass graft disease: Analysis of proliferative activity in human aorto-coronary bypass grafts. Heart Surg Forum. 2002;5 Suppl 4: S331-41.
Hu, et al. Activation of pdgf receptor alpha in vascular smooth muscle cells by mechanical stress. Faseb J. 1998;12(12): 1135-42.
Huynh, et al. Alterations in wall tension and shear stress modulate tyrosine kinase signaling and wall remodeling in experimental vein grafts. J Vasc Surg. 1999;29(2): 334-44.
Huynh, et al. External support modulates g protein expression and receptor coupling in experimental vein grafts. Surgery. 1999;126(2): 127-34.
Igase, et al. Apoptosis and bcl-xs in the intimal thickening of balloon-injured carotid arteries. Clin Sci (Loud). Jun. 1999;96(6): 605-12.
International search report and written opinion dated Sep. 26, 2011 for PCT Application No. US2010/062487.
Izzat, et al. Influence of external stent size on early medial and neointimal thickening in a pig model of saphenous vein bypass graftin. Circulation 1996; 94:1741-5.
Jacot, et al. Early adaptation of human lower extremity vein grafts: Wall stiffness changes accompany geometric remodeling. J Vasc Surg. 2004;39(3): 547-55.
Janowski-Bell, et al. Histology of Blood Vessels—www2.victoriacollege.edu/dept/bio/Belltutorials/Histology%20Tutorial/Blood%20Vessels/Histology_of_Blood_Vessels.html.

(56) References Cited

OTHER PUBLICATIONS

Jeremy, et al. A bioabsorbable (polyglactin), nonrestrictive, external sheath inhibits porcine saphenous vein graft thickening. J Thorac Cardiovasc Surg. 2004;127(6): 1766-72.
Jeremy, et al. Nitric oxide synthase and adenylyl and guanylyl cyclase activity in porcine interposition vein grafts. Ann Thorac Surg. 1997;63(2): 470-6.
Jiang, et al. A novel vein graft model: Adaptation to differential flow environments. Am J Physiol Heart Circ Physiol. 2004;286(1): H240-5.
Jiang, et al. Wall shear modulation of cytokines in early vein grafts. J Vasc Surg. 2004;40(2): 345-50.
Kamenz, et al. Incidence of intimal proliferation and apoptosis following balloon angioplasty in an atherosclerotic rabbit model. Cardiovasc Res. 2000;45(3): 766-76.
Kanjickal, et al. Polymeric sustained local drug delivery system for the prevention of vascular intimal hyperplasia. J Biomed Mater Res A. 2004;68(3): 489-95.
Karayannacos, et al. Late failure in vein grafts: Mediating factors in subendothelial fibromuscular hyperplasia. Ann Surg. 1978;187(2): 183-8.
Kohler, et al. Inhibition of neointimal hyperplasia in a sheep model of dialysis access failure with the bioabsorbable vascular wrap paclitaxel-eluting mesh. J Vasc Surg. 2007;45(5): 1029-1037; discussion 1037-8.
Kohler, et al. The effect of rigid external support on vein graft adaptation to the arterial circulation. J Vasc Surg. 1989;9(2): 277-85.
Labadie, et al. Pulsatile perfusion system for ex vivo investigation of biochemical pathways in intact vascular tissue. Am J Physiol Heart Circ Physiol. 1996;270(2): H760-8.
Lafleur, et al. Activation of pro-(matrix metalloproteinase-2) (pro-mmp-2) by thrombin is membrane-type-mmp-dependent in human umbilical vein endothelial cells and generates a distinct 63 kda active species. Biochem J. 2001;357(Pt 1): 107-15.
Lee, et al. Nanofiber alignment and direction of mechanical strain affect the ECM production of human ACL fibroblast. Biomaterials 2005;26(11):1261-1270.
Lee, et al. Theoretical hydraulic consequences of vein graft taper. Journal of Vascular Surgery. 2003, 38: 785-792.
Levorson, et al. Fabrication and characterization of multiscale electrospun scaffolds for cartilage regeneration. Biomed Mater 2013;8:014103. doi:10.1088/1748-6041/8/1/014103.
Liao, et al. A novel time-varying poly lactic-co glycolic acid external sheath for vein grafts designed under physiological loading. Tissue Eng. 2007;13(12): 2855-62.
Lignen, et al. Tissue inhibitor of matrix metalloproteinases-1 impairs arterial neointima formation after vascular injury in mice. Circ Res. 1999;85(12): 1186-91.
Ligush, et al. Evaluation of endothelium-derived nitric oxide mediated vasodilation utilizing ex vivo perfusion of an intact vessel. J Surg Res. 1992;52(5): 416-21.
Liu, et al. A possible role of initial cell death due to mechanical stretch in the regulation of subsequent cell proliferation in experimental vein grafts. Biomech Model Mechanobiol. 2002;1(1): 17-27.
Liu, et al. Changes in the organization of the smooth muscle cells in rat vein grafts. Ann Biomed Eng. 1998;26(1): 86-95.
Liu, et al. Partial prevention of monocyte and granulocyte activation in experimental vein grafts by using a biomechanical engineering approach. J Biomech. 1999;32(11): 1165-75.
Liu, et al. The signaling protein rho is necessary for vascular smooth muscle migration and survival but not for proliferation. Surgery. 2002;132(2): 317-25.
Mavromatis, et al. Early effects of arterial hemodynamic conditions on human saphenous veins perfused ex vivo. Arterioscler Thromb Vasc Biol. 2000;20(8): 1889-95.
McManus, et al. Electrospun fibrinogen: feasibility as a tissue engineering scaffold in a rat cell culture model. Journal of Biomedical Materials Research Part A 81.2 (2007): 299-309.
McManus, et al. Mechanical properties of electrospun fibrinogen structures. Acta Biomaterialia 2.1 (2006): 19-28.
Mehta, et al. External stenting reduces long-term medial and neointimal thickening and platelet derived growth factor expression in a pig model of arteriovenous bypass grafting. Nat Med. 1998;4(2): 235-9.
Meng, et al. Mechanical stretching of human saphenous vein grafts induces expression and activation of matrix-degrading enzymes associated with vascular tissue injury and repair. Exp Mol Pathol. 1999;66(3): 227-37.
Morinaga, et al. Effect of wall shear stress on intimal thickening of arterially transplanted autogenous veins in dogs. J Vasc Surg. 1985;2(3): 430-3.
Morisaki, et al. Cell cycle-dependent inhibition of DNA synthesis by prostaglandin i2 in cultured rabbit aortic smooth muscle cells. Atherosclerosis. 1988;71(2-3): 165-71.
Moritz et al., A Method for Constricting Large Veins for Use in Arterial Vascular Reconstruction, Artificial Organs, 1990, pp. 394-398, 14(5).
Morton, et al. Electrospun fibrin nanofibers for the use in tissue engineering. Modification of fibrin to improve applications in regenerative medicine (2010): 81.
Mosesson, M. W. Fibrinogen and fibrin structure and functions. Journal of Thrombosis and Haemostasis 3.8 (2005): 1894-1904.
Muluk, et al. Enhancement of tissue factor expression by vein segments exposed to coronary arterial hemodynamics. Journal of Vascular Surgery: Official Publication, the Society for Vascular Surgery Land] International Society for Cardiovascular Surgery, North American Chapter. 1998;27(3): 521-7.
Murphy-Ullrich, et al. Focal adhesion integrity is downregulated by the alternatively spliced domain of human tenascin. J Cell Biol. 1991;115(4): 1127-36.
Murphy-Ulrich, JE. The de-adhesive activity of matricellular proteins: Is intermediate cell adhesion an adaptive state? J Clin Invest. 2001;107(7): 785-90.
Nagai et al., Identification of Two Types of Smooth Muscle Myosin Heavy Chain Isoforms by eDNA Cloning and Immunoblot Analysis, The Journal of Biological Chemistry, Jun. 15, 1989, pp. 9734-9737, 264(17).
Nakazawa, et al. Smooth muscle cell migration induced by shear-loaded platelets and endothelial cells. Enhanced platelet-derived growth factor production by shear-loaded platelets. Int Angiol. 2000;19(2): 142-6.
Nedovic, et al. Cell immobilisation by electrostatic droplet generation. Landbauforsch Volk 2002, (241) 11-17.
Newby, et al. Extracellular matrix degrading metalloproteinases in the pathogenesis of arteriosclerosis. Basic Res Cardiol. 1994;89(Suppl 1): 59-70.
Nikolopoulos, et al. Integrin-linked kinase (ilk) binding to paxillin ldl motif regulates ilk localization to focal adhesions. J Biol Chem. 2001;276(26): 23499-505.
Nishibe, et al. Induction of angiotensin converting enzyme in neointima after intravascular stent placement. Int Angiol. 2002;21(3): 250-5.
Notice of allowance dated Nov. 20, 2015 for U.S. Appl. No. 13/520,009.
Office action dated May 21, 2015 for U.S. Appl. No. 13/520,009.
Parsonnet, et al. New stent for support of veins in arterial grafts. Arch Surg. 1963;87: 696702.
Perumcherry, et al. A Novel Method for the Fabrication of Fibrin-Based Electrospun Nanofibrous Scaffold for Tissue-Engineering Applications. Tissue Engineering Part C: Methods 17.11 (2011): 1121-1130.
Pintucci, et al. Anti-proliferative and anti-inflammatory effects of topical mapk inhibition in arterialized vein grafts. Faseb J. 2006;20(2): 398-400.
Porter, et al. Marimastat inhibits neointimal thickening in a model of human vein graft stenosis. Br J Surg. 1998;85(10): 1373-7.
Porter, et al. Production and inhibition of the gelatinolytic matrix metalloproteinases in a human model of vein graft stenosis. Eur J Vasc Endovasc Surg. 1999;17(5): 404-12.

(56) References Cited

OTHER PUBLICATIONS

Porter, et al. Simvastatin inhibits human saphenous vein neointima formation via inhibition of smooth muscle cell proliferation and migration. J. Vasc. Surg. 2002;36: 150-7.
Porter, et al. The development of an in vitro flow model of human saphenous vein graft intimal hyperplasia. Cardiovasc Res. 1996;31(4): 607-14.
Powell, et al. Matrix-specific effect of endothelial control of smooth muscle cell migration. J Vasc Surg. 1996;24(1): 51-7.
Predel, et al. Implications of pulsatile stretch on growth of saphenous vein and mammary artery smooth muscle. Lancet. 1992;340(8824): 878-9.
Qian, et al. Gene expression of bfgf and intimal hyperplasia of autologous vein grafts in rats. Zhonghua Yi Xue Za Zhi. 1996;76(11): 826-8.
Ramos, et al. Histologic fate and endothelial changes of distended and nondistended vein grafts. Ann Surg. 1976;183(3): 205-28.
Redmond, et al. Effect of pulse pressure on vascular smooth muscle cell migration: The role of urokinase and matrix metalloproteinase. Thrombosis & Haemostasis. 1999;81(2): 293-300.
Reneker, et al. Electrospinning of Nanofibers from Polymer Solutions and Melts. Adv Appl Mech 2007;41. doi:10.1016/S0065-2156(07)41002-X.
Resnick, et al. Hemodynamic forces are complex regulators of endothelial gene expression. The Faseb J. 1995;9(10): 874-82.
Rho, et al. Electrospinning of collagen nanofibers: Effects on the behavior of normal human keratinocytes and early-stage wound healing. Biomaterials. 2006;27(8): 1452-61.
Sage, et al. Extracellular proteins that modulate cell-matrix interactions. Sparc, tenascin, and thrombospondin. J Biol Chem. 1991;266(23): 14831-4.
Sell, et al. Cross-linking methods of electrospun fibrinogen scaffolds for tissue engineering applications. Biomedical Materials 3.4 (2008): 045001.
Severyn, et al. The influence of hemodynamics and wall biomechanics on the thrombogenicity of vein segments perfused in vitro. J Surg Res. 2004;121(1): 31-7.
Shigematsu, et al. Direct and indirect effects of pulsatile shear stress on the smooth muscle cell. Int Angiol. 2000;19(1): 39-46.
Sho, et al. Subnormal shear stress-induced intimal thickening requires medial smooth muscle cell proliferation and migration. Exp Mol Pathol. 2002;72(2): 150-60.
Simosa, et al. Survivin expression is up-regulated in vascular injury and identifies a distinct cellular phenotype. J Vasc Surg. 2005;41(4): 682-90.
Soletti et al., A Bi-layered Elastomeric Scaffold for Tissue Engineering of Small-Diameter Vascular Grafts, Acta Biomater., Jan. 2010, pp. 110-122, 6(1).
Southgate, et al. Involvement of extracellular-matrix-degrading metalloproteinases in rabbit aortic smooth-muscle cell proliferation. Biochem J. 1992288 (Pt 1): 93-9.
Sreerekha, et al. Fabrication of fibrin based electrospun multiscale composite scaffold for tissue engineering applications. Journal of biomedical nanotechnology 9.5 (2013): 790-800.
Stankus, et al. Fabrication of biodegradable elastomeric scaffolds with sub-micron morphologies. J Biomed Mater Res A. 2004;70(4): 603-14.
Stankus, et al. Fabrication of cell microintegrated blood vessel constructs through electrohydrodynamic atomization. Biomaterials. 2007;28:2738-46.
Stankus, et al. Microintegrating smooth muscle cells into a biodegradable, elastomeric fiber matrix. Biomaterials. 2006;27(5): 735-44.
Stitzel, et al. Controlled fabrication of a biological vascular substitute. Biomaterials. 2006, 27: 1088-1094.
Stooker, et al. Perivenous application of fibrin glue reduces early injury to the human saphenous vein graft wall in an ex vivo model. European Journal of Cardio-thoracic Surgery. 2002, 21: 212-217.
Stooker, et al. Pressure-diameter relationship in the human greater saphenous vein. Ann Thorac Surg. 2003;76(5): 1533-8.
Szilagyi, et al. Biologic fate of autogenous vein implants as arterial substitutes: Clinical, angiographic and histopathologic observations in femoro-popliteal operations for atherosclerosis. Ann Surg. 1973;178(3): 232-46.
Tai, et al. Compliance properties of conduits used in vascular reconstruction. Br J Surg. 2000;87(11): 1516-24.
Traver, et al. New Generation Tissue Sealants and Hemostatic Agents: Innovative Urologic Applications. Reviews in Urology. 2006, 8: 104-111.
Tu, et al. Migfilin and mig-2 link focal adhesions to filamin and the actin cytoskeleton and function in cell shape modulation. Cell. 2003;113: 37-47.
Tyagi, et al. Stretch-induced membrane type matrix metalloproteinase and tissue plasminogen activator in cardiac fibroblast cells. J Cell Physiol. 1998;176(2): 374-82.
Uzui, et al. The role of protein-tyrosine phosphorylation and gelatinase production in the migration and proliferation of smooth muscle cells. Atherosclerosis. 2000;149(1): 51-9.
Veazey, et al. Mammalian cell delivery via aerosol deposition. J. Biomed. Mater. Res. 2005 (72B)334-8.
Vijayan, et al. External supports and the prevention of neointima formation in vein grafts. Eur J Vasc Endovasc Surg. 200224(1): 13-22.
Vijayan, et al. Long-term reduction of medial and intimal thickening in porcine saphenous vein grafts with a polyglactin biodegradable external sheath. J Vasc Surg. 2004;40(5): 1011-9.
Vorp, et al. A device for the application of cyclic twist and extension on perfused vascular segments. Am J Physiol Heart Circ Physiol. 1996;270(2): H787-95.
Vorp, et al. Modeling the transmural stress distribution during healing of bioresorbable vascular prostheses. Ann Biomed Eng. 1995;23(2): 178-88.
Wan, et al. Differential, time-dependent effects of perivenous application of fibrin glue on medial thickening in porcine saphenous vein grafts. European Journal of Cardio-thoracic Surgery, 29, (2006): 742-747.
Wang, et al. Expression of apoptosis-related proteins and structural features of cell death in explanted aortocoronary saphenous vein bypass grafts. Cardiovasc Surg. 2001;9(4): 31928.
Wang, et al. Regulation of vein graft hyperplasia by survivin, an inhibitor of apoptosis protein. Arterioscler Thromb Vasc Biol. 2005;25(10): 2081-7.
Weisel, et al. Computer modeling of fibrin polymerization kinetics correlated with electron microscope and turbidity observations: clot structure and assembly are kinetically controlled. Biophysical journal 63.1 (1992): 111.
Weisel, et al. Mechanisms of fibrin polymerization and clinical implications. Blood 121.10 (2013): 1712-1719.
Wesly, et al. Static linear and nonlinear elastic properties of normal and arterialized venous tissue in dog and man. Circulation Research (Online). 1975;37(4): 509-20.
Wnek, et al. Electrospinning of nanofiber fibrinogen structures. Nano Letters 3.2 (2003): 213-216.
Wolf, et al. Antibodies against transforming growth factor-beta 1 suppress intimal hyperplasia in a rat model. J Clin Invest. 1994;93(3): 1172-8.
Wolff, et al. Transforming growth factor-betal antisense treatment of rat vein grafts reduces the accumulation of collagen and increases the accumulation of h-caldesmon. J Vasc Surg. 2006;43(5): 1028-36.
Wu, C. Integrin-linked kinase and pinch: Partners in regulation of cell-extracellular matrix interaction and signal transduction. J Cell Sci. 1999;112 (Pt 24): 4485-9.
Wu, et al. Integrin-linked kinase (ILK) and its interactors: A new paradigm for the coupling of extracellular matrix to actin cytoskeleton and signaling complexes. J Cell Biol. 2001;155(4): 505-10.
Xu, et al. Aligned biodegradable nanofibrous structure: a potential for blood vessel engineering. Biomaterials Feb. 2004; 25(5): 877-86.
Xu, et al. Electrospun Nanofiber Fabrication as Synthetic Extracellular Matrix and Its Potential for Vascular Tissue Engineering. Tissue Engineering, vol. 10, No. 7/8, 2004.

(56) References Cited

OTHER PUBLICATIONS

Yamaoka, et al. Timp-1 production by human scleral fibroblast decreases in response to cyclic mechanical stretching. Opthalmic Research. 2001;33(2): 98-101.

Yu, et al. Electrospinning, Encyclopedia of Polymer Science & Technology (2008) 1-20.

Zhang, et al. Association of smooth muscle cell phenotypic modulation with extracellular matrix alterations during neointima formation in rabbit vein grafts. J Vasc Surg. 1999;30(1): 169-83.

Zilla, et al. Constrictive external nitinol meshes inhibit vein graft intimal hyperplasia in nonhuman primates. The Journal of Thoracic and Cardiovascular Surgery 2008;136:717-725.

Zilla, et al. Utilization of shape memory in external vein-graft meshes allows extreme diameter constriction for suppressing intimal hyperplasia: A non-human primate study. J Vasc Surg 2009;49:1532-42.

Zuckerbraun, et al. Overexpression of mutated IkappaBalpha inhibits vascular smooth muscle cell proliferation and intimal hyperplasia formation. J Vasc Surg. 2003;38(4): 812-9.

Zwolak, et al. Kinetics of vein graft hyperplasia: Association with tangential stress. Journal of Vascular Surgery: Official Publication, the Society for Vascular Surgery [and] International Society for Cardiovascular Surgery, North American Chapter. 1987;5(1): 12636.

European Search Report dated Feb. 20, 2017 for EP Application No. 10841716.3.

\* cited by examiner

CURVILINEAR GRAFT

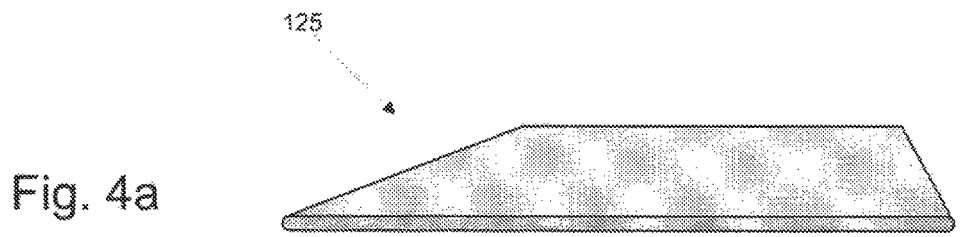
Fig. 4a
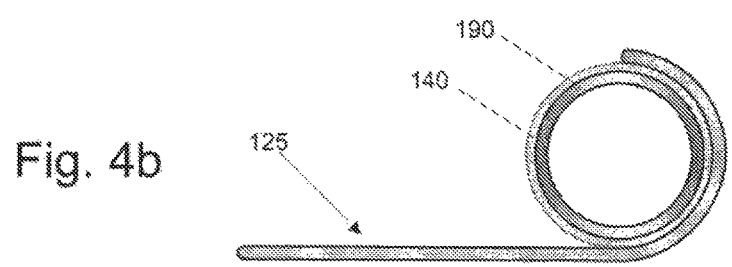
Fig. 4b
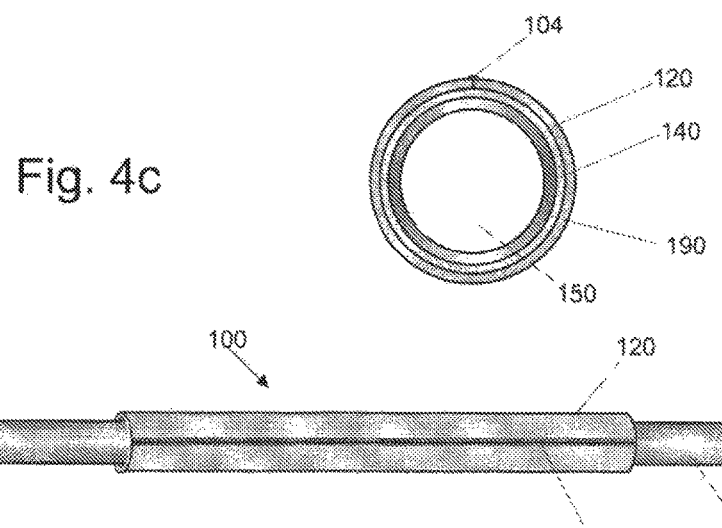
Fig. 4c
Fig. 4d

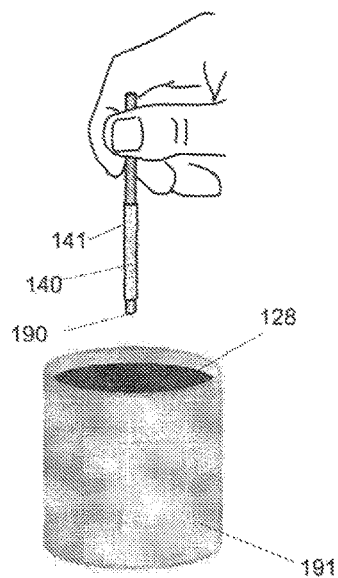
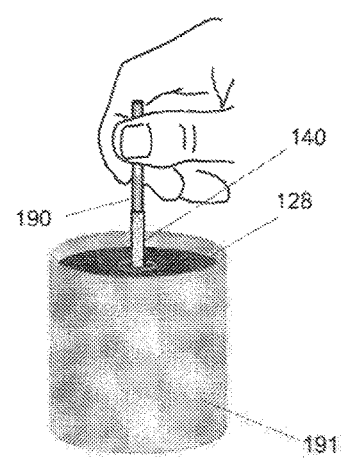
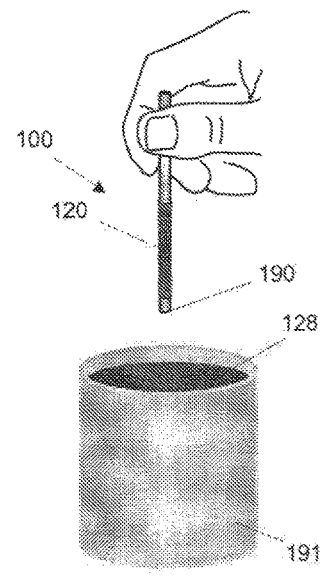
Fig. 12a   Fig. 12b   Fig. 12c
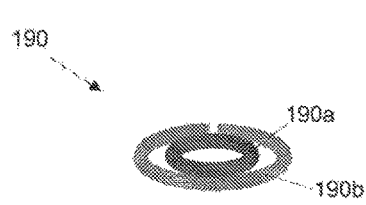
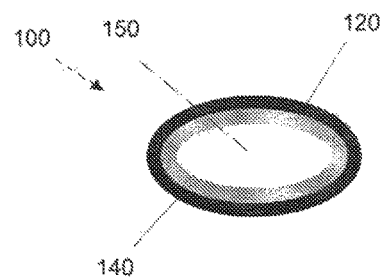
Fig. 12d   Fig. 12e

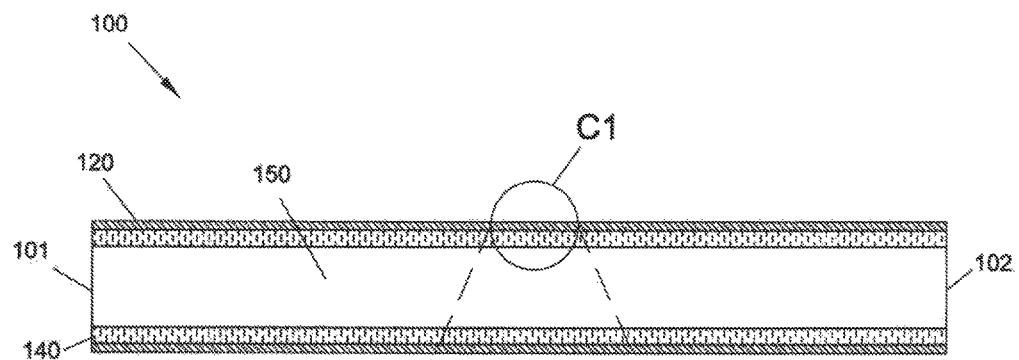
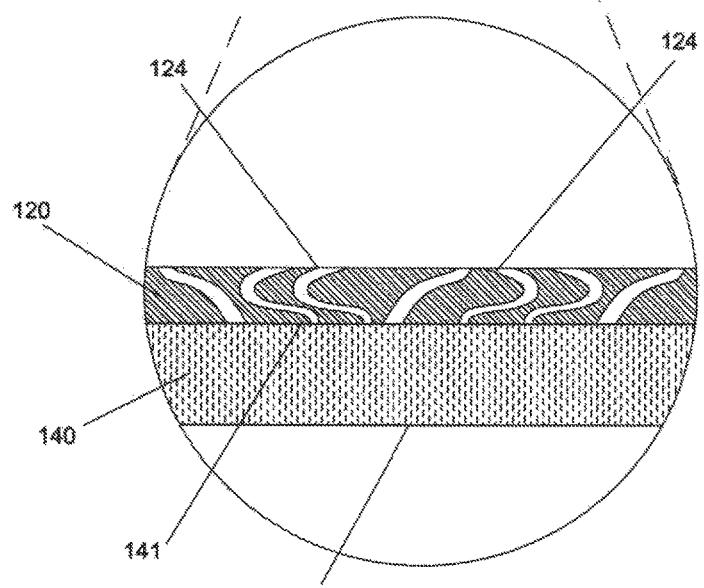

GRAFT DEVICES AND METHODS OF FABRICATION

CROSS REFERENCE

This application is a continuation of U.S. application No. 13/520,009 filed Jul. 20, 2012; which is a National Phase of International Application No. PCT/US2010/062487 filed Dec. 30, 2010; which claims the benefit of priority to U.S. Provisional Patent Application No. 61/291,820 filed Dec. 31, 2009; each of which is hereby incorporated by reference in its entirety.

DESCRIPTION OF THE INVENTION

The present invention relates generally to graft devices for a mammalian patient. In particular, the present invention provides graft devices comprising a flow conduit and a covering.

BACKGROUND OF THE INVENTION

Coronary artery disease, leading to myocardial infarction and ischemia, is currently the number one cause of morbidity and mortality worldwide. Current treatment alternatives consist of percutaneous transluminal angioplasty, stenting, and coronary artery bypass grafting (CABG). CABG can be carried out using either arterial or venous conduits and is the most effective and most widely used treatment to combat coronary arterial stenosis, with nearly 500,000 procedures being performed annually. In addition there are approximately 80,000 lower extremity bypass surgeries performed annually. The venous conduit used for bypass procedures is most frequently fire autogenous saphenous vein and remains the graft of choice for 95% of surgeons performing these bypass procedures. According to the American Heart Association, in 2004 there were 427,000 bypass procedures performed in 249,000 patients. The long term outcome of these procedures is limited due to occlusion of the graft vessel or anastomotic site as a result of intimal hyperplasia (IH), which can occur over a timeframe of months to years.

Development of successful small diameter synthetic or tissue engineered vascular grafts has yet to be accomplished and use of arterial grafts (internal mammary, radial, or gastroepiploic arteries, for example) is limited by the short size, small diameter and availability of these vessels. Despite their wide use, failure of arterial vein grafts (AVGs) remains a major problem: 12% to 27% of AVGs become occluded in the first year with a subsequent annual occlusive rate of 2% to 4%. Patients with failed arterial vein grafts (AVGs) can die or require re-operation.

IH accounts for 20% to 40% of all AVG failures within the first 5 years. Several studies have determined that IH develops, to some extent, in all mature AVGs and this is regarded by many as an unavoidable response of the vein to grafting. IH is characterized by phenotypic modulation, followed by de-adhesion and migration of medial and adventitial smooth muscle cells (SMCs) and myofibroblasts into the intima where they proliferate. In many cases, this response can lead to stenosis and diminished blood flow through the graft. It is thought that IH can be initiated by the abrupt exposure of the veins to the dynamic mechanical environment of the arterial circulation.

For these and other reasons, there is a need for devices and methods which provide enhanced AVGs and other graft devices for mammalian patients. Desirably the devices can improve long term patency and minimize surgical and device complications.

SUMMARY

Developing a reliable means to prevent the early events of the IH process and other luminal narrowing responses can contribute to improvements in the outcome of arterial bypass and other graft procedures. Therefore, provided herein is a method of mechanically conditioning and otherwise treating and/or modifying an arterial vein graft, or any flow conduit (e.g., living cellular structure) or artificial graft, typically, but not exclusively, in autologous, allogeneic, or xenogeneic transplantation procedures. To this end, provided herein is a method of wrapping a (low conduit, including, without limitation, a vein, artery, urethra, intestine, esophagus, trachea, bronchi, ureter, duct and fallopian tube. The graft is wrapped with a covering such as a fiber matrix, typically with a biodegradable (also referred to as bioerodible or bioresorbable) polymer about a circumference of the flow conduit. In one non-limiting embodiment, the matrix is deposited onto flow conduit by electrospinning. In one particular non-limiting embodiment, the flow conduit is a vein, such as a saphenous vein, that is used, for example, in an arterial bypass procedure, such as a coronary artery bypass procedure.

This new approach can have two potential applications. In the first non-limiting application, the matrix can be used as a peri-surgical tool for the modification of vein segments intended for use as an AVG. The modification of the vein or other tubular structure can be performed by treating the structure at bedside, immediately after removal from the body and just prior to grafting. In one non-limiting example, after the saphenous vein is harvested, and while the surgeon is exposing the surgical site, the polymer wrap can be electrospun onto the vein just prior to it being used for the bypass procedure.

The invention, in one aspect, features a graft device that includes a flow conduit and a covering. The flow conduit includes an inner surface, an outer surface, a proximal end, a distal end, and a lumen therethrough. The covering has a thickness and at least one channel extending from at least one of the inner surface or the outer surface of the flow conduit. The at least one channel extends through at least a portion of the thickness of the covering. The graft device is constructed to provide connection between a first body space and a second body space.

In some embodiments, the covering further includes an inner surface and an outer surface The at least one channel can extend from the inner surface to the outer surface of the channel. In some embodiments, the at least one channel has a diameter of approximately 100 microns to 200 microns. The at least one channel can have a length of approximately 100 microns to 1000 microns. In some embodiment, the at least one channel is configured and arranged to induce angiogenesis. The at least one channel can comprise a circuitous route. The at least one channel can comprise a relatively linear route. The relatively linear route can be laser cut. In some embodiments, the at least one channel is constructed and arranged to approximate one or more properties of the vasa vasorem of a vessel. The at least one channel can be created after the covering is applied to the flow conduit. The at least one channel can be created while the covering is applied to the How conduit. In some embodiments, the covering is constructed and arranged to support an anastomotic connection. The covering can be constructed and arranged to support an anastomotic connector.

According to an aspect of the invention, a graft device includes a tubular flow conduit and a covering. The tubular flow conduit includes an inner wall, an outer wait, a proximal end, a distal end, and a lumen from the proximal end to the distal end. The tubular flow conduit is positioned proximate the flow conduit, such as proximate the inner and/or outer walls of the flow conduit. The graft device is constructed and arranged for connection between a first body space and a second body space.

In some embodiments, the tubular flow conduit comprises tissue. Numerous forms of tissue, such as tissue selected from the group consisting of: bone; skin; eustachian tube; artery; vein; urethra; lympathic duct; nasal channel; intestine; esophagus; ureter, urethra; trachea; bronchi; duct; fallopian tube; and combinations of these, can comprise the flow conduit. Tissue can be from a patient receiving the graft device (autologous tissue), from another being of the same species (allogeneic tissue), or tissue from a species different than the patient (xenogeneic tissue). The tubular flow conduit cam be a hollow tissue structure, such as a tissue structure selected from the group consisting of: eustachian tube; artery; vein; urethra; intestine; esophagus; ureter; urethra; trachea; fallopian tube; and combinations of these. The tubular flow conduit can be cultured tissue, such as tissue grown around or within a tubular scaffold, or tissue grown flat and subsequently formed into a tube. Cultured tissue can be grown in-situ, such as within the body of the patient intended to receive the graft device.

In some embodiments, the tubular flow conduit comprises artificial material, solely or in combination with living tissue. Numerous forms of artificial materials can be used, such as materials selected from the group consisting of: polytetrafluoroethylene (PFFE); expanded PTFE (ePTFE); polyester; polyvinylidene fluoride/hexafluoropropylenc (PVDF-HFP); silicone; and combinations thereof.

The covering can be placed lo surround the outer wall of the tubular flow conduit, the inner wall of the tubular flow conduit, or both. The covering can be restrictive, applying a force resistant to radial expansion of the tubular flow conduit, such as by applying a force to initial radial expansion (e.g. when the covering is applied in contact with the tubular flow conduit), or by applying a force after a fixed amount of radial expansion occurs (e.g. when the covering has an inner diameter slightly larger than the outer diameter of the flow conduit). In some embodiments, the tubular flow conduit is a harvested vein, and the covering is applied in a manner compressing the natural inner diameter of the vein, such as compressing to a diameter approximating an artery being bypassed.

The covering can comprise one or more materials, such as one or more polymers. The polymers can be natural or synthetic polymers, or blends of natural and synthetic polymers. Typical polymers include but are not limited to: silk, chitosan, collagen, elastin, alginate, cellulose, polyalkanoates, hyaluronic acid, gelatin; or combinations of these. The covering can be applied to the flow conduit while the flow conduit has a mandrel (e.g. a straight or a curved mandrel) inserted through at least a portion of its lumen.

The covering can comprise a helical spiral, such as a spiral that is uncoiled, expanding its inner diameter to be easily inserted over the tubular flow conduit. The covering can be radially stretched, after which the tubular flow conduit can be inserted and the covering relaxed. The covering can include a cylindrical braid, such that longitudinal shortening of the covering causes its inner diameter to expand. The covering can comprise a wrapped sheet, such as a sheet formed into a tube after which the flow conduit is inserted, or a sheet that is wrapped around the flow conduit while being formed into a tube. The covering cart comprise a tube with a slit along at least a portion of its length. The slit can be matched edge to edge or overlapped around the tubular flow conduit. The slit can be sealed, such as with an adhesive (e.g., fibrin glue), energy (e.g., heat, light or ultrasound energy); and combinations of these. The covering can be constructed and arranged to shrink, such as a radial constriction caused by exposure to heat, light, or a polymerization process.

The covering can include a wrapped fiber, such as an electrospun fiber, or one or more fiber types supplied on one or more spools, and can be wrapped by hand or with a braiding or other wrapping machine. The wrapped fiber can be overlapped over other fibers, and can include attachment points between one or more fibers or between a fiber and the tubular flow conduit. Attachment paints can be at the end of a fiber, or a cross-tie between two fiber mid portions. Attachment points can include fusion of two or more fibers such as with the application of heat, ultrasound or other melting or welding energy. Attachment points can be achieved through the application of a knot or an adhesive such us fibrin glue. Attachment points can be achieved through solvent bonding. Wrapped fibers can be applied in a weave, such as a weave of multiple fibers of similar or dissimilar materials of construction. Typical fiber materials include but are not limited to: silk; polyurethane; PCL; PEUU; PVDF-HFP; and combinations of these. A braid of multiple fibers, such as a fiber braid applied on a spool, can be wrapped about the flow conduit.

The covering can be applied to the flow conduit by dipping the flow conduit one or more times in a liquid material configured to solidify over time. The covering can be applied to the flow conduit using a tool, such as a brush (e.g., a paint brush). Liquid covering materials can be applied with a mandrel inserted into the flow conduit. In some embodiments, an anastomotic connector includes multiple filaments that are braided or otherwise wrapped around the flow conduit, such as with a braiding machine, the covering comprising the wrapped filaments.

The covering can be biodegradable, such as a covering comprising a material that has a biodegradation rate that is based on the amount of stress applied to the covering. The covering can include a semi-permeable membrane surrounding a biodegradable structure, and applied stress can increase permeability of the membrane such as to increase biodegradation. The covering can include microcapsules with porosity proportional to applied stress, the microcapsules releasing a biodegradation inhibitor or accelerator.

The covering can elude an agent, such as a drug. The elution rate can change over time, such as a covering in which oxygen tension determines release of an angiogenic factor, for example a covering in which reduced tension reduces the amount of VEGF released.

The graft device can include a circular cross section such as a circular cross section of relatively constant or varying diameter from its proximal end to its distal end. The graft device can include, along at least a portion of its length, a non-circular cross section such as an elliptical cross section. The covering can be attached to the flow conduit, such as by knitting with a suture or other filaments or with an adhesive. The graft device can have a linear bias or a non-linear bias, in embodiments in which the graft device has a non-linear bias, the non-linear biased geometry can be based on a patient image, such as an image acquired with equipment selected from the group consisting of: X-ray; magnetic resonant imaging device ("MRI"); computed tomography scanning device ("CT-scan"); nuclear magnetic resonance device ("NMR"); ultrasound device; digital camera (e.g. a charge-coupled device ("CCD") camera); film camera; and combinations of these. In embodiments in which the graft device has a non-linear bias, a non-linear mandrel can be inserted into the flow conduit prior to application of the covering, causing a resilient, non-linear bias. A collapsible mandrel, such as an inflatable mandrel or furled mandrel, can be used to ease removal after the covering is applied.

The covering can include one of more channels, such as one or more channels that extend from the inner wall to the outer wall of the covering. Channels can be relatively linear or include tortuous or otherwise circuitous geometries. Channels can be created during and/or after application of the covering to the flow conduit. Channel diameters can be about 100 to about 200 microns, and channel lengths can be about 100 to about 1000 microns.

The covering can include two or more layers. In some embodiments, a three layer covering includes a middle layer mat is constructed and arranged to biodegrade prior to any significant biodegradation of the other two layers.

In some embodiments, the first body space is an aorta and the second body space is a coronary artery. The graft device can be attached to three or more body spaces, in a serial grafting scheme, such as with a connection at the flow conduit's proximal end, distal end and a third location between the flow conduit's proximal end and distal end. The third location can be at a location along the flow conduit including an opening, such as a side branch ostium in embodiments in which the flow conduit is a harvested blood vessel.

The graft device can include a reinforced portion near the proximal or distal ends of the tubular flow conduit. The reinforcement can include a reinforced covering, such as a thickened or otherwise reinforced covering proximate the proximal of distal ends. The graft device can include one end that is modified to include, or be attachable to, an anastomotic clip.

The graft device can include a mandrel, such as a conductive mandrel used to apply the covering to the flow conduit in an electrospinning process. The mandrel can have a multi-planar geometry, such as a geometry matching the geometry of placement of the graft device. The mandrel can be plastically deformable, such as to be formed by a clinician during a surgical implantation procedure. The mandrel can be constructed and arranged to transition from a rigid to a flexible state, and/or from a flexible state to a rigid state, such as a mandrel constructed of a material selected from the group consisting of: a low melting point metal such as indium; a shaped memory metal; a shaped memory polymer, a liquid crystal that changes rigidity when current is applied; and combinations of these.

The invention, in another aspect, features a method of creating & graft device. A tubular flow conduit is selected. The flow conduit comprises an inner wall, an outer wall, a proximal end, a distal end, and a lumen therethrough. A covering is applied proximate the flow conduit. The flow conduit can be placed around a mandrel, such as a mandrel which is shaped to match a portion of a patient's anatomy. The mandrel can be shaped prior to and/or during the implantation procedure. The mandrel can be shaped based on a patient image.

The covering can comprise fibers, such as fibers supplied on spools or fibers created during an electrospinning process. Fiber from multiple spools (e.g., similar or dissimilar fibers) can be applied proximate the flow conduit. The spooled fiber can be applied by hand or by a machine such as a braiding machine. The fiber can be applied in a cross-hatch or other weave pattern, and can be applied in one or more passes across the flow conduit. One or more fiber ends, or mid portions of a fiber, can be fixed to the flow conduit or another fiber portion, such as fixation with energy (e.g., to melt the fiber), solvent (e.g., to solvent bond fibers together), or adhesive (e.g., fibrin glue).

The covering can be a liquid material applied to the flow conduit and then solidified or partially solidified. The liquid covering can be applied in a dipping process, or through use of a tool such as a brush or spray tool. The covering can be cross-linked after application.

The covering can be stretched or expanded prior to application proximate the flow conduit. In some embodiments, the covering is a helix which is unwound to radially expand, after which it is positioned proximate the flow conduit. In another embodiment, the covering is a cylindrical braid, and the covering is longitudinally shortened, after which it is positioned proximate the flow conduit. In some embodiments, the covering includes a tube with a slit along at least a portion of its length, and the slit's width is extended after which the covering is positioned proximate the flow conduit, such as when the flow conduit is inserted into the slit.

The flow conduit can be placed onto a mandrel prior to the placing of the covering proximate the flow conduit. The mandrel can be a multi-planar mandrel, such as a three dimensional mandrel created based on a patient image.

The covering can be shrunk after application of the covering, such as by exposure to heat, light of a polymerization process. The covering can be modified such as to increase the porosity of the covering. The graft device can be modified such as to cut one or more ends of the graft device, such as a cut at an oblique angle. An anastomotic connector can be added to the graft device, such as a connector added prior to or after applying the covering proximate the flow conduit. The anastomotic connector can be attached to the covering and/or the flow conduit, or to a location between the covering and the flow conduit.

One or more channels can be created in a portion of the device, such as during and/or after application of the covering. The channels can extend through the covering and/or through the flow conduit. The channels can be relatively linear or have a circuitous path, and can be created using a laser or etching process.

The invention, in another aspect, features a method of creating a graft device. A patient image is produced, and the graft device is created based on the patient image. The graft device can comprise a flow conduit and covering proximate the flow conduit. The flow conduit can be placed on a mandrel, such as a mandrel based on the patient image. The covering can be applied to the flow conduit with the patient image based mandrel inserted into the flow conduit. The mandrel can have one or more geometric parameters based on the patient image. The parameters can be selected from the group consisting of: length; shape, diameter, and combinations of these.

The invention, in another aspect features a method of creating a graft device. A three dimensional mandrel is produced, and a graft device is created over the three dimensional mandrel. The graft device can comprise a flow conduit and covering proximate the flow conduit. The flow conduit can be placed on a mandrel, such as a mandrel based on the patient image. The covering is applied to the flow conduit with the patient image based mandrel inserted into the flow conduit. The mandrel can have one or more geometric parameters based on the patient image. The parameters can be selected from the group consisting of: length; shape, diameter, and combinations of these.

BRIEF DESCRIPTION OF THE DRAWINGS

The accompanying drawings, which are incorporated in and constitute a part of this specification, illustrate various embodiments of the present invention, and together with the description, serve to explain the principles of the invention. In the drawings:

FIG. 4a illustrates a perspective view of a sheet of covering material, consistent with the current invention;

FIG. 4b illustrates a flow conduit with an inserted mandrel being covered with the sheet of covering material of FIG. 4a, consistent with the current invention;

FIGS. 4c and 4d illustrate end and side views, respectively, of a graft device, including an adhesive seal along the edges of the covering, consistent with the present invention;

FIGS. 12a, 12b and 12c illustrate a series of sequential flow conduit dipping steps used in the fabrication of yet another embodiment of a graft device, consistent with the present invention;

FIG. 12d illustrates an end view of a two piece mandrel with an elliptical cross section and a split outer portion and used in the fabrication steps of FIGS. 12a, 12b and 12c, consistent with the present invention;

FIG. 12e illustrates and end view the graft device fabricated using the dip method of FIGS. 12a, 12b and 12c and the mandrel of FIG. 12d, consistent with the present invention;

FIG. 14 illustrates a graft device including multiple channels, consistent with the present invention;

FIG. 14a illustrates a magnified view of a portion of the graft device of FIG. 14;

DETAILED DESCRIPTION OF THE DRAWINGS

Figure 1A:
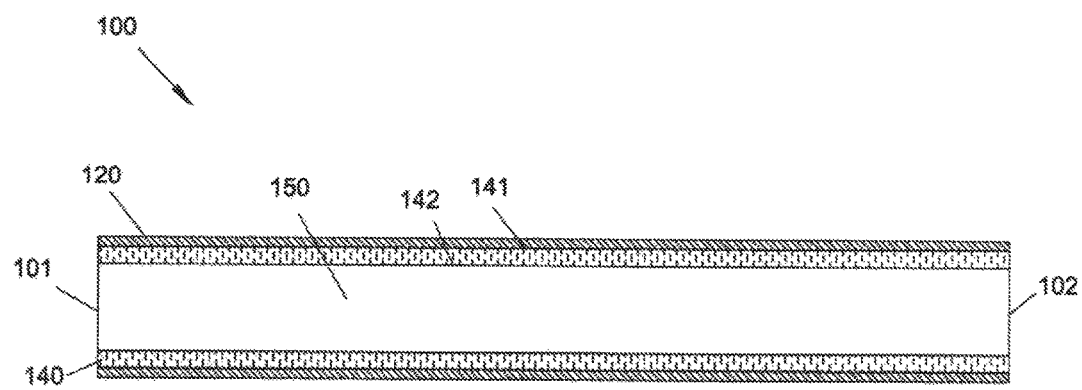
FIGS. 1a and 1b illustrate side and end sectional views, respectively, of a graft device including a flow conduit and a covering, consistent with the current invention.

Reference will now be made in detail to the present embodiments of the invention, examples of which are illustrated in the accompanying drawings. Wherever possible, the same reference numbers will be used throughout the drawings to refer to the same or like parts, Provided herein is a graft device including a flow conduit und covering, such as a graft device for connection between a first body space and a second body space. The flow conduit can comprise tissue, such as autologous, allogeneic, or xenogeneic tissue, including, without limitation: vein; artery; urethra; intestine; esophagus; ureter; trachea; bronchi; duct tissue; fallopian tube; or combinations of these (meaning the entire structure or a portion of those tissues). The flow conduit can also be a tissue engineered vascular graft, comprised of a covering material (biological- or synthetic-based) that is seeded with adult differentiated cells and/or undifferentiated stem cells, or unseeded. The covering can be treated with synthetic, biological, or biomimetic cues to enhance anti-thrombogenicity or selective or non-selective cell repopulation once implanted in vivo. Alternatively or additionally, the flow conduit can include an artificial, non-tissue, structure, such as polytetrafluoroethylene (PTFE); expandable PTFE (cPTFE); polyester; polyvinylidene fluoride/hexafluoropropylene (PVDF-HFP); silicone; and combinations of these. The flow conduit can have a relatively uniform cross section, or a cross section that varies (e.g. in diameter or cross sectional geometry) along the length of the flow conduit. Additional graft devices, systems and methods are also described in applicant's co-pending U.S. Provisional Patent Application Ser. No. 61/286,820, filed Dec. 16, 2009, entitled "Graft Devices and Methods for Use," which is incorporated by reference herein in its entirety.

Also provided is a method of creating a graft device by modifying a tubular flow conduit through the application of a covering. One or more fibers, typically supplied on spools, can be wrapped around the flow conduit. A fiber matrix can be applied to the flow conduit, such as via an electrospinning process. A liquid covering, such as a liquid polymer (a polymer solution, a polymer suspension, or a polymer melt) or other liquid material, can be applied to the flow conduit in liquid (non-fibrous) form, which then solidifies or partially solidifies over time. The flow conduit can be dipped into the liquid material, or the liquid material can be applied to the flow conduit with a tool such as a brush or a spraying device. Typical polymers include natural polymers, synthetic polymers, and blends of natural and synthetic polymers. For example and without limitation, natural polymers include silk, chitosan, collagen, elastin, alginate, cellulose, polyalkanoates, hyaluronic acid, or gelatin. Natural polymers can be obtained from natural sources or can be prepared by synthetic methods (including by recombinant methods) in their use in the context of the technologies described herein. Non-limiting examples of synthetic polymers include: homopolymers, heteropolymers, co-polymers and block polymers or co-polymers.

As used herein, the descriptor "flow conduit" does not refer specifically to a geometrically perfect tube having a constant diameter and a circular cross -section. It also embraces tissue and artificial conduits having non-circular and varying cross sections, and can have a variable diameter, and thus any shape having a contiguous wall surrounding a lumen (that is, they are hollow), and two openings into the lumen such that a liquid, solid or gas can travel from one opening to the other.

The covering typically is substantially or essentially contiguous about an internal or external wall of a flow conduit, meaning that the covering forms a continuous, supportive ring on a surface and about a circumference of a portion, but not necessarily over the entire surface (e.g., length) of the flow conduit. The covering can be "restrictive", meaning that the covering is in substantial contact with the outer surface of the flow conduit, or the covering can be narrowly spaced and proximate to the outer surface of the flow conduit (e.g. to restrict after an initial unrestricted expansion). The covering can also be "constrictive", meaning that the diameter of the flow conduit is reduced by the application of the covering. Restrictive coverings can be used to reinforce, restrict, hinder and/or prevent substantial circumferential expansion of the flow conduit, such as when the graft device is used as a bypass graft and is exposed to arterial pressure; or otherwise when the flow conduit is radially expanded. The degree of restriction by the covering typically is such that when exposed to internal pressure, such as typical arterial pressures, the flow conduit is prevented from distending to the extent that would occur without such restriction. Constrictive coverings can be used to match the internal diameter of the flow conduit, to the internal diameter of the target tissue being connected by the flow conduit. For example, quite often a vein being used as a coronary artery bypass graft has a considerably larger internal diameter than the target coronary artery being bypassed. In order to reduce flow disturbances, it is advantageous to match the internal diameter of the graft (flow conduit) to the internal diameter of the stenosed coronary artery. The covering can be durable or temporary, such as when the restrictive nature of a biodegradable covering can decline over time. The covering can have a relatively uniform cross section, or a cross section that varies along the length of the covering.

The covering can be applied to a flow conduit which has either a cylindrical or non-cylindrical mandrel inserted in its lumen. Mandrels are typically constructed and arranged to be removed from the graft device of the present invention without damaging the flow conduit or any other portion of the graft device. The mandrel can comprise an expandable tube, such as a furled tube or other radially expandable structure, such that the mandrel can be unfurled or otherwise radially constricted for atraumatic removal from the flow conduit of the graft device. The mandrel can transform from a rigid state to a flexible state, and vice versa.

The mandrel can be relatively straight, or can have a non-linear geometry, such as a throe dimensional geometry intended to match anatomical locations of a patient, such as an anatomical topography proximate two or more intended anastomotic connections for the graft device. The mandrel can be a malleable or otherwise deformable structure which is shaped during a patient open surgical procedure. Alternatively, the mandrel can be fabricated based upon one or more patient images created during an imaging procedure, such as an imaging procedure selected from the group consisting of: X-ray; MRI, CT scan, NMR, ultrasound, CCD camera; film camera; and combinations of these.

In coverings applied to a flow conduit with an electrospinning process, an electrically conductive mandrel, for example a rod that is formed of a conductive material such as stainless steel, can be placed inside a tubular conduit, such as a vein, and polymer fibers deposited about the circumference of at least a portion of the tissue by rotation or other movement of the mandrel, movement of the nozzles supplying the fiber, and/or movement of the electrical field directing the fibers toward the mandrel. A thickness of the covering can be controlled by adjusting the chemical or physical properties of the polymer solution to be deposited, increasing the infusion rate of the polymer solution, and/or adjusting duration of the electrospinning. Use of more viscous polymer composition can result in thicker fibers, requiring less time to deposit a covering of a desired thickness. Use of a less viscous polymer composition can result in thinner fibers, requiring increased deposition time to deposit a covering of a desired thickness. The thickness of the covering and fibers within the covering affects the speed of biodegradation of the covering. Biodegradation can also be varied by altering the surface finish or porosity of the fibers, which can be altered by using solvents or diluents that evaporate at varying rates or also by adding purifiers to the solution, such as immiscible fluids, emulsified panicles or undissolved solids that can be later dissolved, thereby creating pores. These parameters are optimized, depending on the end-use of the covering, to achieve a desired or optimal physiological effect. Thickness can be varied along the length of a target in a regular or irregular fashion, such as in creating a target that is thicker at one or both ends, in the center or as with a location-dependent symmetrical or asymmetrical thickness. In another particular embodiment, the thickness is varied by moving an electrospinning nozzle back and forth slowly, near a specific circumferential location, thereby depositing more material proximate to that area. In yet another particular embodiment, covering thickness is determined by the thickness of the flow conduit, such as when the covering is thicker at a circumferential portion of the flow conduit that is thinner than other circumferential portions of the flow conduit.

Electrospinning can be performed using two or more nozzles, wherein each nozzle can be a source of a different polymer solution. The nozzles can be biased with different biases or the same bias in order to tailor the physical and chemical properties of the resulting non-woven polymeric mesh. Additionally, multiple different targets (e.g. mandrels) can be used. When the electrospinning is to be performed using a polymer suspension, the concentration of the polymeric component in the suspension can also be varied to modify the physical properties of the matrix. For example, when the polymeric component is present at relatively low concentration, the resulting fibers of the electrospun non-woven mesh have a smaller diameter than when the polymeric component is present at relatively high concentration. Without any intention to be limited by this theory, it is believed that lower concentration solutions have a lower viscosity, leading to faster flow through the orifice to produce thinner fibers. One skilled in the an can adjust polymer solution chemical and physical properties and process parameters to obtain fibers of desired characteristics, including fibers whose characteristics change along the length or width of the target.

Coverings can be constructed and arranged in a manner specific to a patient morphological or functional parameter. These parameters can be selected from the group consisting of: vessel size such as diameter, length, and/or wall thickness; taper or other geometric property of a harvested vessel or vessel intended for anastomotic attachment; size and location of one or more side branch ostium or antrum within the harvested vessel; patient age or sex; vessel elasticity or compliance; vessel vasculitis; vessel impedance; specific genetic factor or trail; and combinations of these.

Coverings of arterial vein grafts can be processed in a way to achieve a certain blood flow rate or shear stress within the treated arterial vein graft. In a typical configuration, shear stress within the arterial vein graft is between about 2-30 dynes/cm$^2$, preferably about 12-20 dynes/cm$^2$. Coverings can be processed in a way to control the oxygen, nutrients, or cellular permeabilities between the extravascular tissues and the abluminal surface of the treated hollow tissue. Such permeabilities depend on the covering chemical and physical properties, the pore size distribution, porosity, and pore interconnectivity. Generally, oxygen, nutrients, and cellular (e.g., endothelial cells, endothelial progenitor cells, etc.) permeability are required to improve the treated hollow tissue in vivo remodeling and healing process. To this, end, the pore size range is typically between about 10 and about 1000 microns, preferably between about 200 and about 500 microns, and the porosity range typically between about 50% and about 95%, preferably between about 60% and about 90%. The pores preferably are highly interconnected so that a relatively straight path along the radial direction of the fiber matrix can be traced from most of the pores across the total thickness of the matrix. Polymers used are typically hydrophilic.

Radial restriction and constriction of saphenous vein grafts has been achieved with stent devices placed over the vein prior to anastomosing the graft to the targeted vessels. The devices of the present invention provide numerous advantages over the stent approaches. The devices of the present invention can have one or more parameters easily customized to a parameter of the harvested vessel and/or another patient parameter. The covering can be customized to a harvested vessel parameter such as geometry, such as to reduce the vein internal diameter to produce desired flow characteristics. The covering can be customized to a target vessel parameter (e.g., the aorta and diseased artery), such as to be compatible with vessel sizes and/or locations. The covering can be modified to simplify or otherwise improve the anastomotic connections, such as lo be reinforced in the portion of the device that is anastomosed (e.g., portion where suture and/or clips pass through) and/or to protrude beyond the length of the flow conduit and overlap other members connected to the graft device.

The devices of the present invention can be made to a wide array of lengths during the procedure, without the need for cutting, such as the cutting of a stent device, which might create dangerously sharp edges. The covering is applied to the flow conduit in a controlled, repeatable manner, by an apparatus such as an electrospinning instrument. The ends of the covering are atraumatic, avoiding tissue damage at the anastomotic sites. In addition, the coverings of the present invention are easily and atraumatically removable, such as to apply another covering. Stent devices are applied manually by a clinician, require significant manipulation which could cause iatrogenic damage, have issues with reproducibility and accuracy limitations, and are difficult to repostion or remove, particularly without damaging the harvested vessel.

As used herein, the term "polymer composition" is a composition comprising one or more polymers. As a class, "polymers" includes homopolymers, heteropolymers, co-polymers, block polymers, block co-polymers and can be both natural and synthetic. Homopolymers contain one type of building block, or monomer, whereas co-polymers contain more than one type of monomer. For example and without limitation, polymers comprising monomers derived from alpha-hydroxy acids including polylactide, poly(lactide-co-glycolide), poly(L-lactide-co-caprolactone), polyglycolic acid, poly(dl-lactide-co-glycolide), poly(l-lactide-co-dl-lactide); monomers derived from esters including polyhydroxybutyrate, polyhydroxyvalerate, polydioxanone and polygalactin; monomers derived from lactones including polycaprolactone; monomers derived from carbonates including polycarbonate, polyglyconate, poly(glycolide-co-trimethylene carbonate), poly(glycolide-co-trimethylene carbonate-co-dioxanone); monomers joined through urethane linkages, including polyurethane, poly(ester urethane) urea elastomer.

A biodegradable polymer is "biocompatible" in that the polymer and degradation products thereof are substantially non-toxic, including non-carcinogenic, non-immunogenic and non-sensitizing, and are cleared or otherwise degraded in a biological system, such as an organism (patient) without substantial toxic effect. Non-limiting examples of degradation mechanisms within a biological system include chemical reactions, hydrolysis reactions, and enzymatic cleavage. Biodegradable polymers include natural polymers, synthetic polymers, and blends of natural and synthetic polymers. For example and without limitation, natural polymers include silk, fibrin, chitosan, collagen, elastin, alginate, cellulose, polyalkanoates, hyaluronic acid, or gelatin. Natural polymers can be obtained from natural sources or can be prepared by synthetic methods (including by recombinant methods) in their use in the context of the technologies described herein. Non-limiting examples of synthetic polymers include: homopolymers, heteropolymers, co-polymers and block polymers or co-polymers.

The polymer or polymers typically will be selected so that it degrades in situ over a time period to optimize mechanical conditioning of the tissue. Non-limiting examples of useful in situ degradation rates include between about 2 weeks and about 1 year, and increments of about 1,2, 4, 8, 12, and 24 weeks therebetween. Biodegradation can occur at different rates along different circumferential and/or axial portions of the covering. A biodegradation rate of the polymer covering can be manipulated, optimized or otherwise adjusted so that the covering degrades over a useful time period. For instance, in the case of a coronary artery bypass, it is desirable that the covering dissolves over about 12 hours or more, typically two weeks or more, so as to prevent substantial sudden stress on the graft. The polymer degrades over a desired period of time so that the mechanical support offered by the polymer covering is gradually reduced over that period and the vein would be exposed to gradually increasing levels of circumferential wall stress (CWS).

The biodegradable polymers useful herein also can be elastomeric. Generally, any elastomeric polymer that has properties similar to that of the soft tissue to be replaced or repaired is appropriate. For example, in certain embodiments, the polymers used to make the wrap are highly distensible. Non-limiting examples of suitable polymers include those that have a breaking strain of from about 100% to about 1700%, more preferably between about 200% and about 800%, and even more preferably between about 200% and about 400%. Further, it is often useful to select polymers with tensile strengths between about 10 kPa and 30 MPa, more preferably between about 5 MPa and 25 MPa, and even more preferably between about 8 and about 20 MPa. In certain embodiments, the elastic modulus calculated for physiologic levels of strain is between about 10 kPa to about 100 MPa, more preferably between about 500 kPa and about 10 MPa, and even more preferably between about 0.8 MPa and about 5 MPa.

In a preferred embodiment, the graft devices of the present invention perform or is produced by one or more parameters listed in Table 1 immediately herebelow, typically with an electrospinning or other material application process:

TABLE 1

| Category | Typical and Preferred Settings |
| --- | --- |
| Covering Material: Applicable Polymers | Typical: PEUU (2-30%); PCL (5-35%); PCL:PGA/PLLA (5-35% - from 80:20 to 50:50); PCL:PLLA (5-35% - from 80:20 to 50:50); PVDF; PVDF-HFP; Silk-Fibroin Preferred: PEUU (5-10%); PCL (5-15%); PCL:PGA (5-15% - 50:50); PCL:PLLA (5-15% - 50:50); PVDF; PVDF-HFP; Silk-Fibroin |
| Covering Process: Solvents (e.g., electrospin solvents, solvents for dipping, or brush application) | Typical: HFIP; DMSO; Chloroform; THF; DMF; Dichloromethane; DMAC, Dioxane; Toluene; Water; Acetone; Methanol; Propanol; Ethanol; Lithium Bromide; Aqueous Solutions (alkaline/acidic) Preferred: HFIP; DMF; THF; DMSO; Water More Preferred HFIP; Water |
| Covering Thickness | Typical: 50-1000 µm Preferred: 50-200 µm More Preferred: 50-150 µm |
| Covering $O_2$ Permeability | Typical $10^{-10}$ to $10^{-6}$ $(cm^2\ mL\ O_2)/(s\ mL\ mmHg)$ |
| Covering Porosity | Typical 50%-95% Preferred 85%-90% |
| Covering average Pore Size | Typical 0.001-2.0 mm Preferred 0.10-1.0 mm Also Preferred 0.005-0.020 mm |
| Covering Compliance (measured in arterial-like conditions 70-110 mmHg) | Typical 2-100 × $10^{-4}$ $mmHg^{-1}$ Preferred (arterial blood applications) 2-15 × $10^{-4}$ $mmHg^{-1}$ |
| Covering Anastomotic Retention Force (e.g., suture retention) | Typical 1-10N |
| Covering Circumferential Elastic Modulus (Static Elastic Modulus E) | Typical 0.5-2.0 MPa Preferred 0.8-2.0 MPa |
| Covering Viscoelasticity (Dynamic Elastic Modulus G) | Typical between 1-fold and 2-fold E |
| Covering Degradation Kinetics (in vivo complete resorption) | Typical greater than 2 weeks Preferred linear reduction over 3-6 months |
| Covering Hardness | Typical polymer Brinnell Scale between 5 and 40 |
| Covering Roughness | Typical 2-50 µm |

As used herein, the terms "comprising," "comprise" or "comprised," and variations thereof, are meant to be open ended. The terms "a" and "an" are intended to refer to one or more.

As used herein, the term "patient" or "subject" refers to members of the animal kingdom including but not limited to human beings.

As used herein, a "fiber" comprises an elongated, slender, thread-like and/or filamentous structure.

As used herein, a "matrix" is any two- or three-dimensional arrangement of elements (e.g., fibers), either ordered (e.g., in a woven or non-woven mesh) or randomly-arranged (as is typical with a mat of fibers typically produced by electrospinning).

A polymer "comprises" or is "derived from" a stated monomer if that monomer is incorporated into the polymer. Thus, the incorporated monomer that the polymer comprises is not the same as the monomer prior to incorporation into a polymer, in that at the very least, certain terminal groups are incorporated into the polymer backbone. A polymer is said to comprise a specific type of linkage if that linkage is present in the polymer.

Figure 1B:
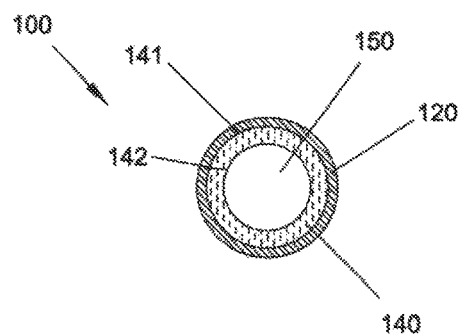

Referring now to FIGS. 1a and 1b, side sectional and end sectional views, respectively, of a graft device of the present invention are illustrated. Graft device 100, biased in a relatively linear bias as shown, includes lumen 150 from first end 101 to second end 102. Graft device 100 also includes flow conduit 140 which is surrounded on its outer wall 141 by covering 120. Alternatively or additionally, covering 120 can surround the inner wall 142 of flow conduit 140. Covering 120 can be a radially restrictive covering, such as a radially restrictive covering comprising a fiber matrix applied to flow conduit 140 during an electrospinning process. A restrictive covering can be used to limit radial expansion of flow conduit 140, such as when device 100 is used as a bypass graft in a cardiac bypass procedure. Similarly, the covering 120 can be radially constrictive, such as a radially constrictive covering comprising a fiber matrix applied to flow conduit 140 during an electrospinning process. Covering 120 can be radially stretched prior to application around flow conduit 140, such as with a tube expanding device. Covering 120 can be radially shrunk after placement around flow conduit 140, such as when covering 120 is a material constructed and arranged to radially shrink with the application of heat, light or polymerization. Flow conduit 140 can include any tissue or artificial structure, such as has been described hereabove, or can include both tissue and artificial materials.

Graft device 100 is constructed and arranged to be placed between a first body space, such as a source of oxygenated arterial blood such as the aorta, and a second body space, such as a location distal to an occluded artery, such as an occluded coronary artery. In a typical embodiment, flow conduit 140 is a harvested vessel, such as a harvested saphenous vein graft (SVG). Graft device 100 can be processed after the application of covering 120. This processing can include cutting one or both of ends 101 and 102, such as to cut to a particular length. The cutting can be performed orthogonally or at an oblique angle (e.g. a spatulation cut), such as to improve creation and/or longevity of an anastomosis. The processing can include modifying one or both of flow conduit 140 and covering 120, such as to modify a surface or other parameter of flow conduit 140 or covering 120. Porosity can be modified, such as with a laser drilling device or mechanical puncturing device. Surface properties can be modified, such as with a User or other etching process.

Covering 120 can have one or both of its end portions (portions proximate end 101 and end 102) modified or otherwise of different construction than the mid portion of covering 120. In a particular embodiment, at least one end portion of covering 120 is modified lo support an anastomotic connection such as a connection achieved with suture, staples, or an anastomotic connector. The modification can include the end portions of covering 120 being thicker or thinner than the mid portion; the end portions being constructed of a different material or materials such as the inclusion of an increased tear resistant material such us the inclusion of a metal mesh; and combinations of these.

Flow conduit 140 can be biodegradable or include one or more biodegradable portions. Biodegradation of flow conduit 140 can be stress or strain dependent biodegradation. Stress or strain dependent degradation (hereinafter "stress dependent degradation") kinetics of covering 120 can be customized for a desired remodeling of flow conduit 140, such as when flow conduit 140 is a harvested vessel such as a harvested saphenous vein graft. Stress based degradation can be used such that degradation would occur or accelerate only when mechanical support would be no longer desired (this degradation arrangement could be relatively continuous or triggered by a threshold). In certain embodiments, covering 120 is used to provide temporary mechanical support to a tissue based flow conduit 140 that is subjected to supra-physiologic conditions. The desired degradation mechanism would be constructed and arranged as follows: device 100 is placed between a first body space such as the aorta, and a second body space, such as a coronary artery. After this implantation, the initial levels of stress applied to covering 120 are at a maximum as the underlying flow conduit 140 (e.g. a harvested vessel) has not yet adapted (e.g. example walls have not yet thickened) and has minimum contribution toward stress relief. The initial degradation rate can be configured to be minimal at this initial stage. As the tissue begins to remodel constructively in response to the increased stress (e.g. vessel tissue training), the stress relief provided by flow conduit 140 will be increased, resulting in lesser stress transmission to covering 120. Covering 120 is constructed and arranged to trigger a mechanism by which the degradation of the material would be accelerated, and with increased degradation would follow increased tissue training, consequential increased degradation, and so on.

In a particular embodiment, covering 120 is a matrix comprising a polymeric network possessing functional groups acting as pan of a polymer backbone and/or as crosslinking molecules for the network. The functional groups are designed to dissociate from the polymer in the presence of naturally occurring enzymes in vivo. The functional groups also possess a receptor for a synthetic molecule (ligand) which is stored in microcapsules embedded at strategic locations, and with a specific distribution, within the matrix. The wall of the microcapsule has a permeability that is directly proportional to the level of stress or strain applied to the wall. A reaction is achieved where higher stress yields larger pores; larger pores yields higher permeability; and higher permeability yields higher release of ligands. In the presence of the synthetic ligands released by the microcapsules, the receptor of the functional group creates a steric hindrance for the naturally occurring enzymatic cleavage resulting in a reduced degradation rate.

In one application, covering 120 with stress based biodegradation surrounds a tissue based flow conduit 140 that is initially damaged but subjected to physiologic demands and therefore in need of temporary support while the healing process takes place. In another embodiment, a semi-permeable membrane surrounds a biodegradable covering 120, and the membrane pores expand under stress to increase biodegradation.

Covering 120 can be constructed and arranged to have stress based responses other than biodegradation, such us chemical, biological, or other responses. Alternative or additional to degradation based kinetics, covering 120 can achieve other response kinetics such as other mechanical response kinetics, electrical response kinetics, drug eluting kinetics, or another type of reaction kinetics. In one exemplary application, graft device 100 is sensitized to the local levels of oxygen tension that controls the kinetics of release of angiogenic factors such as VEGF. Initially, low oxygen tension yields high VEGF release; high VEGF release yields high angiogenesis; high angiogenesis yields higher oxygen tension which then causes lower release of VEGF.

Figure 2:
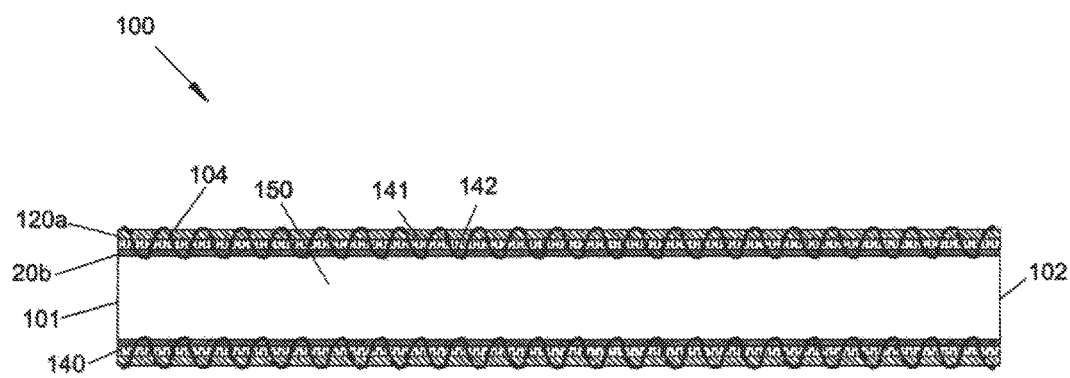
FIG. 2 illustrates a side sectional view of a graft device including a flow conduit with inner and outer covering portions, and a securing filament, consistent with the current invention.

Referring now to FIG. 2, a side sectional view of a graft device of the present invention including a covering with inner and outer portions is illustrated. Graft device 100, biased in a relatively linear bias as shown, includes lumen 150 from first end 101 to second end 102. Graft device 100 also includes flow conduit 140 which is surrounded on its outer wall 141 by covering first portion 120a, and surrounded on its inner wall 142 by covering second portion 120b. Covering first portion 120a and covering second portion 120b are fixedly secured to flow conduit 140 by filament 104, illustrated in a stitching pattern reciprocally passing from the external surface of covering first portion 120a to lumen 150. In an alternative embodiment, filament 104 passes between covering first portion 120a and flow conduit 140 without passing through covering second portion 120b. In another alternative embodiment, filament 104 passes between flow conduit 140 and covering second portion 120b without passing through covering first portion 120a, Alternatively or additionally, an adhesive or other fixation device can be used to mechanically fix covering portion 120a or covering portion 120b to flow conduit 140.

Figure 3:
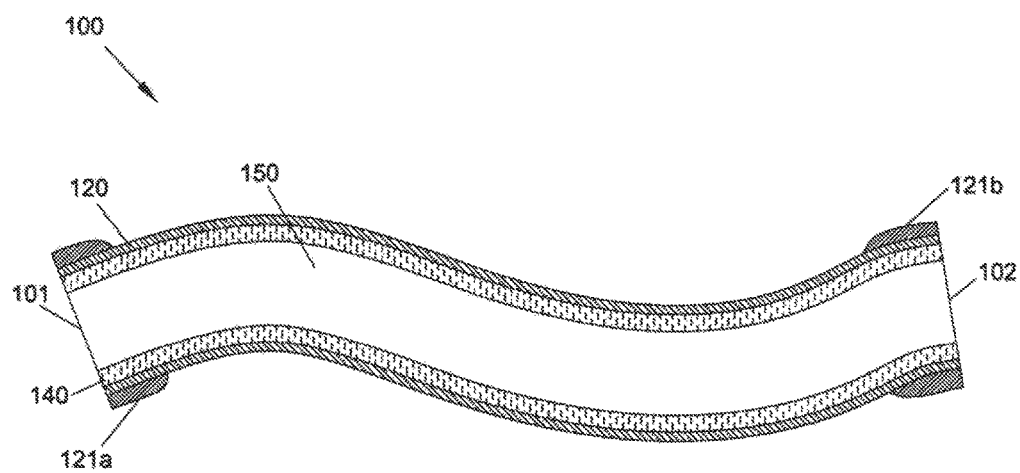
FIG. 3 illustrates a side sectional view of a graft device including a non-linear bias, consistent with the current invention.

Referring now to FIG. 3, a side sectional view of a graft device of the present invention including a curvilinear bias is illustrated. Graft device 100, biased in the curvilinear bias as shown, includes lumen 150 from first end 101 to second end 102. Graft device 100 also includes flow conduit 140 which is surrounded on its outer wall 141 by covering (20. In a particular embodiment, the curvilinear bias of graft device 100 is achieved by the application of covering 120 to flow conduit 140. The curvilinear bias can be achieved by inserting a curvilinear mandrel (not shown but described in detail in reference to FIGS. 18a and 18b hereinbelow), and applying covering 120 with flow conduit m the curvilinear geometry of the inserted mandrel such that a curvilinear bias is achieved. The curvilinear orientation of graft device 100 can be desirable to match a patient condition, such as the anatomical geometry of the area in which graft device 100 is to be placed. The curvilinear geometry can be based on a patient image, such as an image created by an instrument selected from the group consisting of: X-ray; MRI, CT scan, NMR, Ultrasound, CCD camera; film camera; and combinations of these.

Covering 120 includes reinforced ends 121a and 121b. Ends 121a and 121b have a thickness greater than, the mid portion of covering 120. such that an anastomotic connection is reinforced, as has been described above. Ends 121a and 121b can have similar or dissimilar thicknesses. Alternatively or additionally, different materials can be used in ends 121a and 121b, such as tear resistant materials. Ends 121a and 121b can be configured to biodegrade, at similar or dissimilar rates to each other and the mid portion of covering 120.

Referring now to FIGS. 4a through 4d, multiple views of a method for creating a graft device of the present invention are illustrated. FIG. 4a illustrates a perspective view of sheet 125. Sheet 125 can comprise tissue, such as cultured tissue, tissue engineered material, artificial material, such as PTFE or one or more polymer materials described above, or combinations of these. FIG. 4b illustrates an end view of sheet 125 partially rolled around flow conduit 140 which surrounds inserted mandrel 390. FIG. 4c illustrates an end view of covering 120, comprising sheet 125 of FIG. 4b in a tubular geometry and fixedly attached along its longitudinal edges with filament 104. Filament 104 is typically a suture or other biocompatible filamemt used to sew tissue and/or artificial materials together for medical implants or in medical procedures. Covering 120 circumferentially surrounds flow conduit 140 with inserted mandrel 190. FIG. 4d illustrates a side view of graft device 100 of FIG. 4c. In subsequent steps, not shown, mandrel 190 is removed, and device 100 placed between a first body space and second body space as has been described in detail above.

Figure 5:
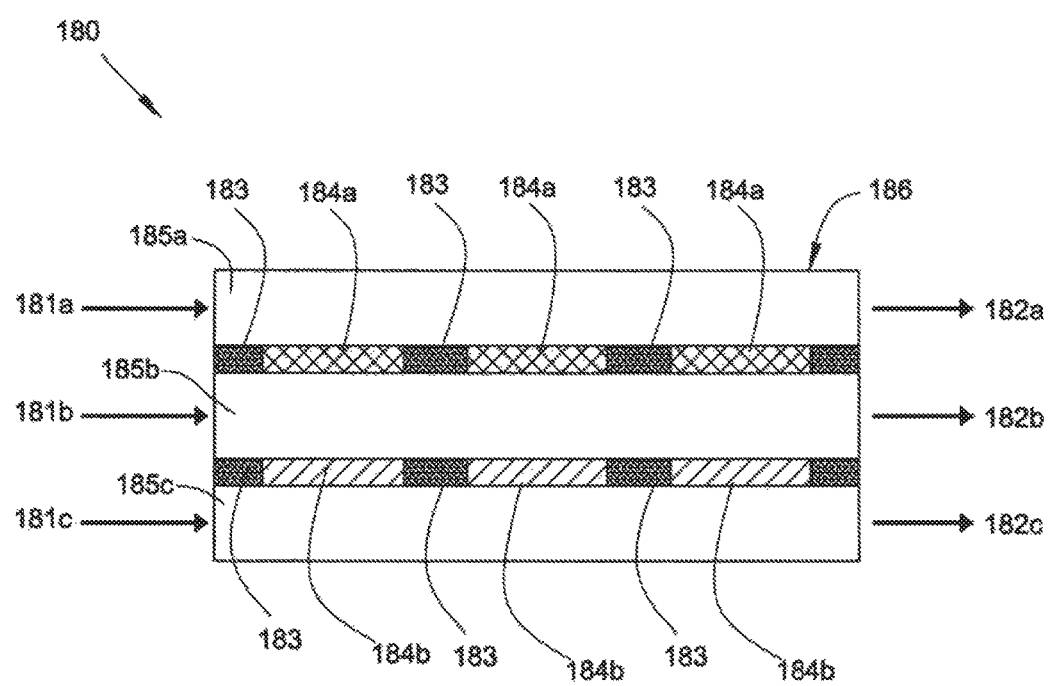
FIG. 5 illustrates a side sectional view of a bioreactor device; consistent with the present invention.

Referring now to FIG. 5, a side sectional view of a bioreactor device of the present invention is illustrated. Bioreactor 180 is constructed and arranged for cell culture. Cellular structures can be generated in or around scaffolds, such as scaffolds implanted in the patient to receive the graft device of the present invention, or a surrogate mammal or other member of the animal kingdom. The cellular structures can be generated as a tube, flat plate, rolled tube or other structure, and used as the flow conduit of the present invention. The patient's body can be used as an "in vivo bioreactor" to grow living tissues as it provides cells and the correct environment (temperature, pH, nutrients) to foster new tissue formation. For example, bioreactor 180 or another biocompatible "template" such as a PTFE or a metal mandrel can be inserted into a body cavity (e.g., the abdominal cavity) for a determined amount of time (e.g., a few days to a few weeks). Autologous, allogeneic or xenogeneic tissues can be generated. Advantages include the natural foreign body response which tends to "encapsulate" an object implanted in an area with good vascularization.

Bioreactor 180 includes cell support scaffold 184a and 184b configured to allow cellular growth thereupon. Bioreactor 180 further includes upper channel 185a, middle channel 185b and low channel 185c, through which an inoculum can be introduced, as well as cell nourishing nutrients. Each channel 185a, 185b and 185c includes inlets 181a, 181b and 181c respectively. Each channel 185a, 185b and 185c further includes outlets 182a, 182b and 182c respectively. The first 184a and second 184b cell support scaffolds each comprise at least one three-dimensional porous matrix, such as a matrix containing non-woven fibrous polyethylene terephthalate or a similar material. The first scaffold 184a is positioned within chamber 186 between upper channel 185a and middle channel 185b. The second scaffold 184b is positioned between middle channel 185b and lower channel 185c.

First scaffold 185a and second scaffold 185b can have similar or dissimilar thicknesses and can have similar or dissimilar porosities. These differences can be based on the type of cell being deposited and cultured in the particular matrix. Alternatively or additionally, in order to influence movement of seeded cells into the or through scaffolds 184a and 184b, at least one of the three channels 185a, 185b and 185c can contain a fluid having one or more cell growth factors, or other cell attractants or repellents. Specific cells can be selected from a mixed population of cells and attracted into scaffold 184a and/or 184b for attachment and growth. Alternatively or additionally, at least one of the three channels 184a, 185b and 185c can contain a cell nourishing medium, such as a gel medium.

Bioreactor 180 preferably has a chamber 186 which is elongated, having the three channels 185a, 185b and 185c extending through a lengthwise extent of chamber 186. Each channel's inlet 181a, 181b and 181c, respectively, is positioned at a first lateral periphery of chamber 186, and each channel's outlet 182a, 182b and 182c. respectively, is positioned at a second lateral periphery of chamber 186 and generally opposite the first lateral periphery. First scaffold 184a and second scaffold 184b can be separated from each other by non-scaffold material 183, as shown in FIG. 5.

In typical use, bioreactor 180 includes chamber 186 wherein the middle channel 185b contains a fluid carrying a plurality of cell types, wherein the upper channel 185a contains a fluid having one or more factors effective for influencing migration of at least a first cell type from middle channel 185b into the first scaffold 184a, and wherein the lower channel 185e contains a fluid having one or more factors effective for influencing migration of at least a second cell type from middle channel 185b into the second scaffold 184b. It is understood that at least one of the three channels 185a, 185b and 185c contains an inoculum comprising cells.

Those skilled in the art will understand that the number of channels 185a, 185b and 185c, and/or scaffolds 184a and 184b can be increased. Multiple bioreactors 180 can be connected via a connector, such as to increase cell culture productivity. A reservoir, not shown but preferably including a fluid medium, can be connected to one or more bioreactors 180, such as to pump or otherwise deliver the flow medium therethrough. One or more valves, also not shown, can be included to control the flow of the flow medium through one or more bioreactors 180. Those skilled will recognize that through the use of a sufficient number of valves, the flew rate of fluid through of each channel can be controlled appropriately for cell seeding, for cell growth and culture, and for cell removal from the bioreactor.

Figures 6A, 6B:
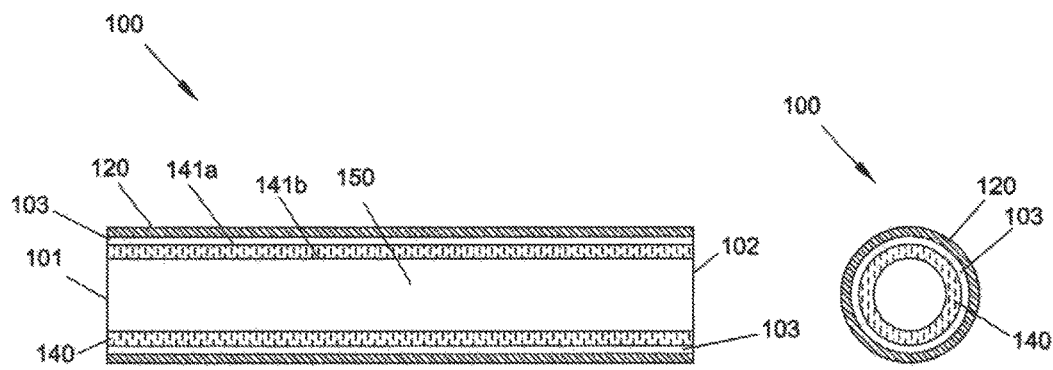
FIGS. 6a and 6b illustrate side and end sectional views, respectively, including a flow conduit surrounded by a covering with a void area between the flow conduit and covering, consistent with the present invention.

Referring now to FIGS. 6a and 6b, side and sectional views, respectively, of a graft device of the present invention configured for delayed restriction of a flow conduit are illustrated. Graft device 100, biased in a relatively linear bias as shown, includes lumen 150 from first end 101 to second end 102. Graft device 100 also includes flow conduit 140 which is surrounded on its outer wall 141a by covering 120. Alternatively or additionally, covering 120 can surround the inner wall 141b of flow conduit 140. Separating outer wall 141a and covering 120 is space 103, sized to allow a fixed amount of expansion of flow conduit 140 prior to applying a restrictive force to flow conduit 140. Space 103 can be configured to ease insertion of flow conduit 140 into covering 120. Covering 120 can be a temporary radially restrictive covering, such as a biodegradable covering. Flow conduit 140 can include any tissue or artificial structure, such as has been described above, or can include both tissue and artificial materials. In an alternative embodiment, covering 120 is shrunk after placement around flow conduit 140, such as to reduce or eliminate space 103.

Figures 7A, 7B, 7C:
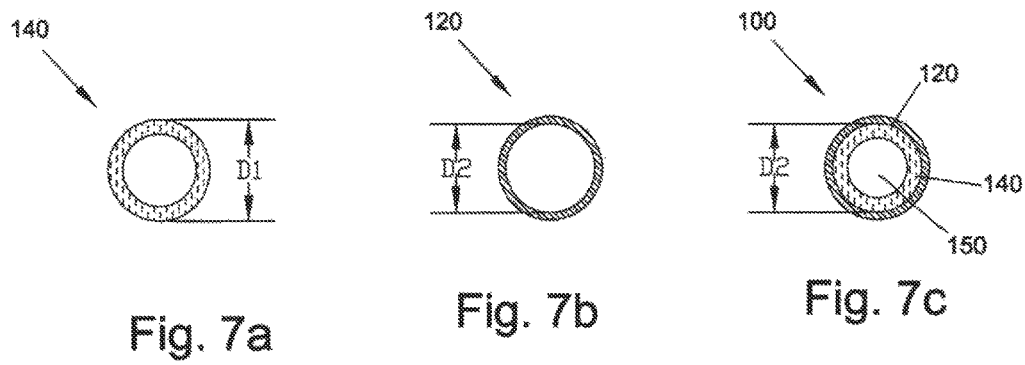
FIG. 7a illustrates an end sectional view of a flow conduit, consistent with the present invention.
FIG. 7b illustrates an end sectional view of a covering, including an inner diameter less than the outer diameter of the flow conduit of FIG. 7a, consistent with the present invention.
FIG. 7c illustrates an end sectional view of a graft device including the flow conduit of FIG. 7a surrounded by the covering of FIG. 7b, consistent with the present invention.

Referring now to FIGS. 7a through 7c, end views of a flow conduit, a covering, and a graft device, respectively, of the present invention are illustrated. FIG. 7a illustrates an end sectional view of a flow conduit 140 with an outer diameter D1. FIG. 7b illustrates an end sectional view of a covering 120 with an inner diameter D2, wherein D2 is less than D1. FIG. 7c illustrates an end sectional view of graft device 100 including flow conduit 140 of FIG. 7a surrounded by covering 120 of FIG. 7b. The outer diameter of flow conduit 140 has been reduced to diameter D2 due to the radial constraint of covering 120, This diameter reduction can be chosen such that a predetermined inner diameter of flow conduit 140 is achieved, such as an inner diameter based on the pre-harvesting diameter of a saphenous vein graft used for flow conduit 140.

Figure 8A:
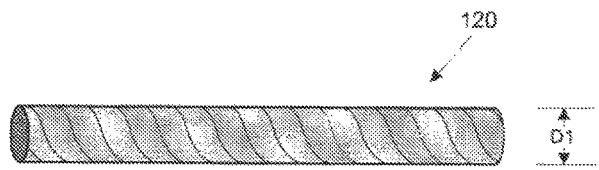
FIG. 8a illustrates a side view of a helical covering, consistent with the present invention.
Figure 8B:
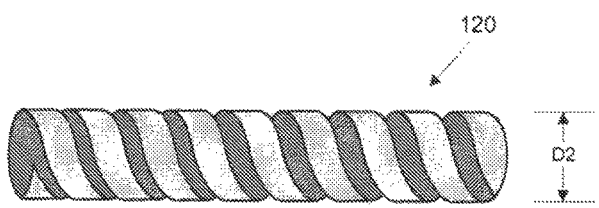
FIG. 8b illustrates a side view of the helical covering of FIG. 8a partially unwound to increase the diameter of the covering, consistent with the present invention.
Figure 8C:
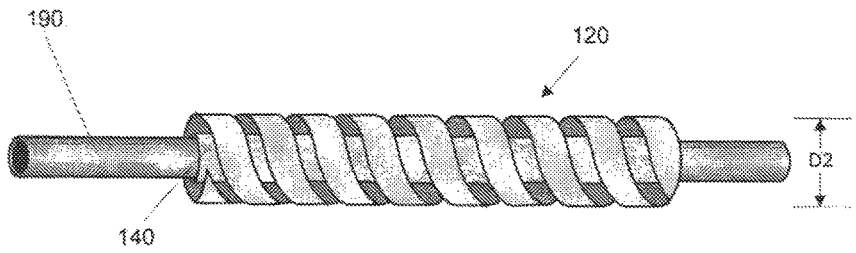
FIG. 8c illustrates a side view a flow conduit with an inserted mandrel having been inserted into the partially unwound helical covering of FIG. 8b, consistent with the present invention.
Figure 8D:
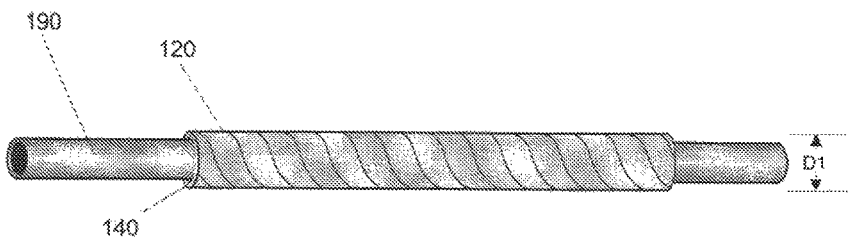
FIG. 8d illustrates a side view of a graft device including the assembly of FIG. 8c after the helical covering has been rewound to the diameter of FIG. 8a, consistent with the present invention.

Referring now to FIGS. 8a through 8d, multiple views of a method for creating a graft device of the present invention are illustrated. FIG. 8a illustrates a side view of covering 120, a helical structure in its relaxed state with an inner diameter D1. FIG. 8b illustrates a side view of covering 120 of FIG. 8a with its helical coil unwound such that covering 120 has increased inside diameter D2. FIG. 8c illustrates a side view of covering 120, maintained in an unwound state with the increased internal diameter D2 of FIG. 8b. inserted over flow conduit 140. Flow conduit 140 has been inserted over mandrel 190. In FIG. 8d, covering 120 has been released or otherwise rewound to diameter D1 of FIG. 8a. such that covering 120 contacts flow conduit 140, such as to radially constrict flow conduit 140. In subsequent steps, not shown, mandrel 190 is removed, and device 100 is placed between a first body space and second body space as has been described in detail above. In an alternative embodiment, mandrel 190 is removed prior to the diameter reduction of covering 120 In another alternative embodiment, flow conduit 120 is temporarily radially expanded, such as with a balloon or other elongate radial expansion device, without unwinding a helical coil, and placed around flow conduit 140. Covering 120 can be constructed of biodegradable material or can include one or more biodegradable portions.

Figure 9A:
FIG. 9a illustrates a side sectional view of a cylindrically braided covering, consistent with the present invention.
Figure 9B:
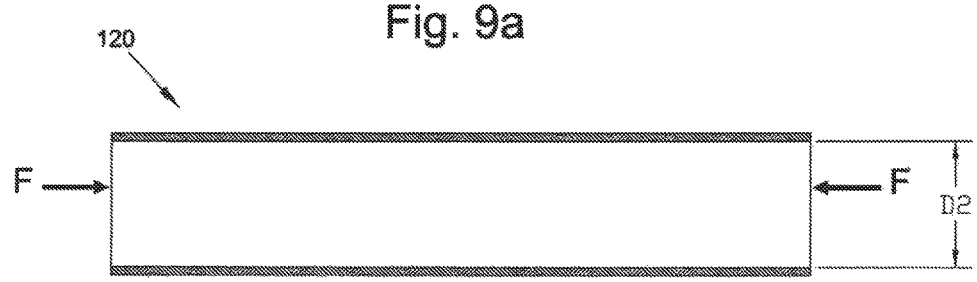
FIG. 9b illustrates a side sectional view of the covering of FIG. 9a after a force has been applied to each end to cause the diameter of the covering to increase, consistent with the present invention.

Referring now to FIGS. 9a through 9d, multiple views of a method for creating a graft device of the present invention are illustrated. FIG. 9a illustrates a side view of covering 120, a cylindrically braided structure in its relaxed state with an inner diameter D1. FIG. 9b illustrates a side view of covering 120 of FIG. 9a with a force F applied to its ends such that covering 120 has increased inside diameter D2. Covering 120 can include a biaxial cylindrical braid. Pushing on the ends of covering 120 shortens its length and increases its diameter. Pulling on the ends of covering 120 causes lengthening as well as a decrease in diameter. The length is gained by reducing the angle between the warp and weft threads of the braid at their crossing points, but this reduces the distance between them and hence the circumference.

Figure 9C:
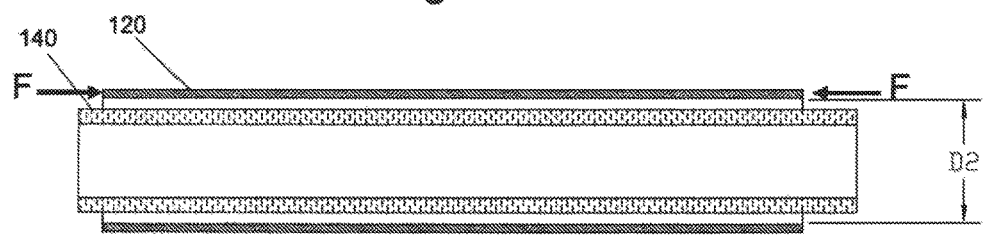
FIG. 9c illustrates a side sectional view a flow conduit having been inserted into the expanded diameter covering of FIG. 9b, consistent with the present invention.
Figure 9D:
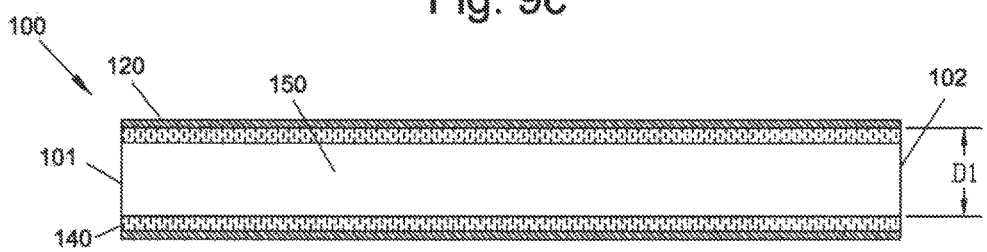
FIG. 9d illustrates a side sectional view of a graft device including the assembly of FIG. 9c after the covering diameter has been reduced, consistent with the present invention.

FIG. 9c illustrates a side view of covering 120, with force F maintained on each end maintaining the increased internal diameter D2 of FIG. 9b. inserted over flow conduit 140. In FIG. 8d. covering 120 has been released (force F removed) to diameter D1 of FIG. 9a, such that covering 120 contacts flow conduit 140, such as to radially constrict flow conduit 140. Graft device 100 includes lumen 150 extending from first end 101 and second end 102 In subsequent steps, not shown, device 100 is placed between a first body space and second body space as has been described in detail hereabove.

Figure 10A:
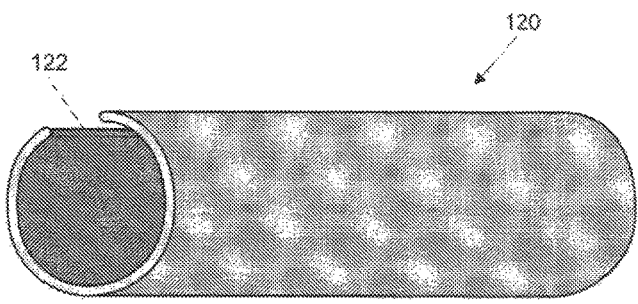
FIG. 10a illustrates a perspective view of a covering including a longitudinal slit, consistent with the present invention.
Figure 10B:
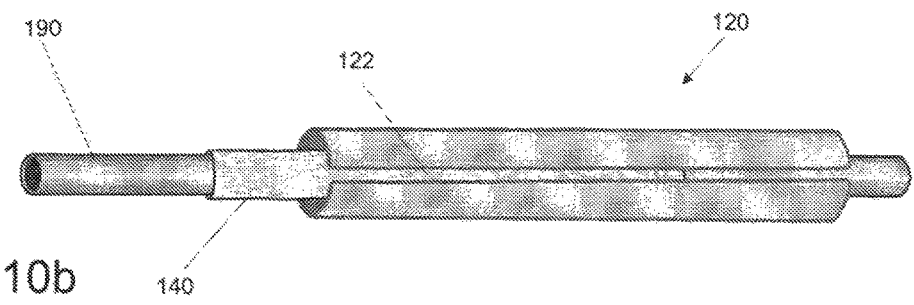
FIG. 10b illustrates a perspective view of a flow conduit with an inserted mandrel having been inserted through the slit of the covering of FIG. 10a, consistent with the present invention.
Figure 10C:
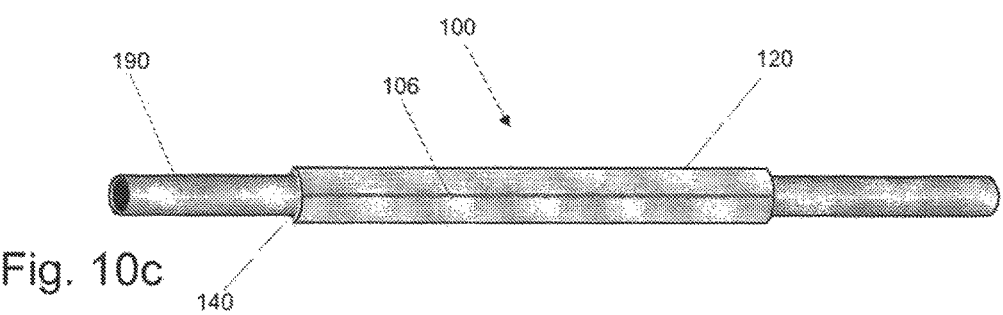
FIG. 10c illustrates aside view of a graft device including the assembly of FIG. 10b after the covering diameter has been reduced and an adhesive applied to an edge of the longitudinal slit, consistent with the present invention.

Referring now to FIGS. 10a through 10c, multiple views of a method for creating a graft device of the present invention are illustrated. FIG. 10a illustrates a side view of covering 120, a tubular structure with longitudinal slit 122 along its length. In an alternative embodiment, slit 122 extends along a partial length of covering 120. FIG. 10b illustrates a side view of covering 120 of FIG. 10a with flow conduit 140 having been inserted through slit 122. Flow conduit 140 surrounds mandrel 190. In an alternative embodiment, slit 122 is pulled apart such that flow conduit 140 can be inserted into either end of covering 120. FIG. 10c illustrates a side view of mandrel 190 with device 100 surrounding it. Slit 122 has been scaled along its length with adhesive 106, preferably a fibrin glue or other biocompatible adhesive. Alternatively or additionally, slit 122 can be sewn together with suture or other biocompatible filament. Alternatively or additionally, slit 122 can be fixed together through the application of energy or exposure to a solvent. Slit 122 can be sealed by overlapping the two longitudinal sides of covering 120, the scaling performed with one or more of: adhesive such as fibrin glue; mechanical fasteners; application of energy such as heat, light or ultrasound energy; and exposure to a covering material solvent. Covering 120 can be radially shrunk, such as via exposure to heat or light, or polymerization of covering 120. In subsequent steps, not shown, mandrel 190 is removed, and device 100 is placed between a first body space and second body space as has been described in detail hereabove. In an alternative embodiment, mandrel 190 is removed prior to the diameter reduction of covering 120.

Figure 11A:
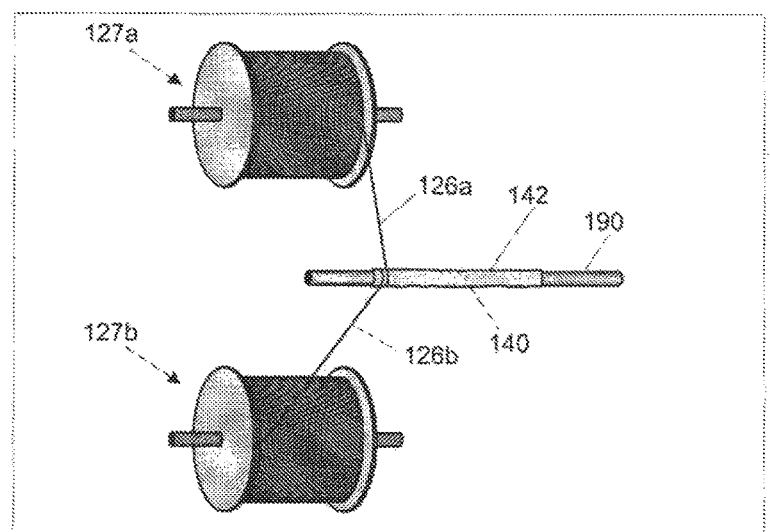
FIGS. 11a and 11b illustrate a method of making a graft device including multiple spools arranged to supply elongate fibers that are circumferentially wrapped around a flow conduit with an inserted mandrel, consistent with the present invention.
Figure 11B:
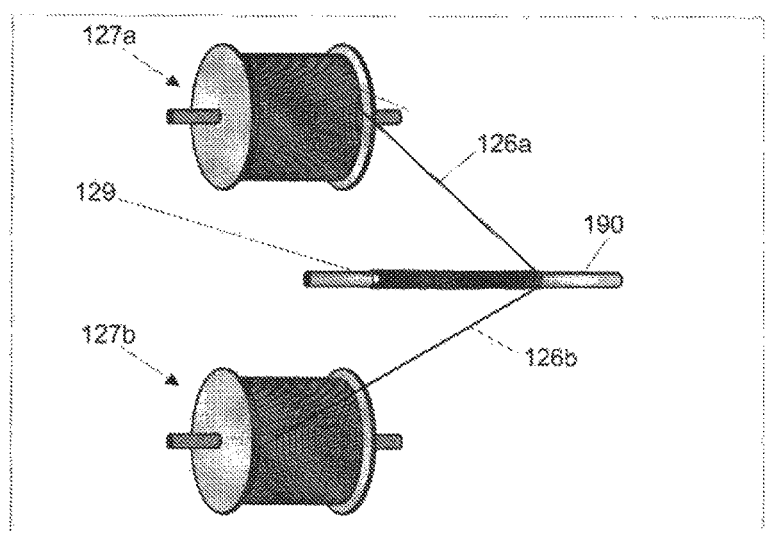
Figure 11C:
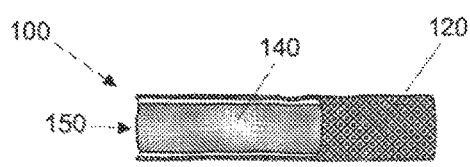
FIG. 11c illustrates a side, partial sectional view of a graft device fabricated with fibers from the multiple spools of FIGS. 11a and 11b, consistent with the present invention.

Referring now to FIGS. 11a through 11c, multiple views of a method for creating a graft device of the present invention are illustrated. FIG. 11a illustrates a side view of flow conduit 140 with inserted mandrel 190. Fibers 126a and 126b are being supplied by spools 127a and 127b, respectively, and are being circumferentially disposed about the outer wall 142 of flow conduit 140. Fibers 126a and 126b can be similar or dissimilar. In an alternative embodiment, a single fiber is used. The process can be performed in a sterile setting, such as an operating room sterile area, or a sterilization step can be performed after application of fibers 126a and 126b around flow conduit 140. FIG. 11b illustrates the view of FIG. 11a after fibers 126a and 126b have substantially covered outer wall 142 of flow conduit 140. Bonding element 129 is included to fixedly attach fibers 126a and/or 126b another portion of the same fiber, the other fiber, and/or flow conduit 140. Bonding element can be included at multiple locations, to affix or create cross-tics between fibers 126a and/or 126b. Bonding element can comprise one or more of: an adhesive such as fibrin glue or elastomeric adhesive, one or more knots; and a melted or solvent bonded joint of the fibers.

Fibers 126a and 126b can be constructed of one or more materials such as silk, polyurethane, PCL, PEUU, PVDF-HFP or other biocompatible material manufactured in a filamentous structure, such as via wet spinning. Fibers 126a and 126b can be a braided fiber. Fibers 126a and 126b can be manually wrapped about flow conduit 140 or an instrument, such as a braiding machine, can be used to spin mandrel 190 and/or rotate spools 127a and 127b about flow conduit 140. Fibers 126a and 126b can be applied in a woven or cross hatch geometry, and multiple passes can be used to overlap the fibers.

In FIG. 11c, a side, partial sectional view of the graft device produced in FIGS. 11a and 11b is illustrated. Covering 120 includes the wrapped fibers 126a and 126b. Graft device 100 includes lumen 150 within flow conduit 140, through which one or more solids, liquids and/or gases can flow.

Referring now to FIGS. 12a through 12c, multiple views of a method for creating a graft device of the present invention are illustrated. FIG. 12a illustrates a side view of flow conduit 140 including outer wall 141 and inserted mandrel 190. Flow conduit 140 is positioned above a reservoir 191 containing liquid covering material 128. Liquid covering material 128 can include numerous liquid polymers, elastomers, or other liquid or suspension materials that are constructed and arranged for application of a biocompatible substance to a structure via a dipping process subsequent to which material 128 hardens or otherwise solidifies. In a typical embodiment, liquid covering material 128 is selected from the group consisting of: a liquid silicone material, such as a silicone gel such as Sylgard; a hyrdrogel such as a fibrin gel; gelatin; and combinations of these. FIG. 12b illustrates of side view of the flow conduit 140 of FIG. 12a having been partially immersed m the liquid covering material 128 of reservoir 191- FIG. 12c illustrates a side view of flow conduit 140 with inserted mandrel 190 once again positioned above reservoir 191. Covering 120 has been formed, or partially formed, during the dipping step of FIG. 12b. Additional dipping steps can be performed, including but not limited to: switching the end of mandrel 190 that is held during the dip; rotating mandrel 190 during a dip or between a first dip and a second dip; treating the dipped flow conduit 140 such as treating with light, heat, air, a cross linking operation, and other exposures to cause liquid material 128 to solidify; and combinations of these.

Referring additionally to FIGS. 12d and 12e, mandrel 190 comprises a split outer portion 190a and a continuous inner portion 190b. both comprising a continuous, relatively elliptical cross section along their length. Mandrel portion 190a is configured to radially expand when mandrel portion 190b is inserted therein. As shown in FIG. 12e, device 100 of FIGS. 12c and 12e has a relatively uniform, elliptical cross section along its length due to the geometry of mandrel 190. The elliptical geometry can provide numerous benefits including but not limited to a preferred bending moment of device 100. Mandrel 190 has been removed from device 100 of FIG. 12e such as by first removing inner portion 190b, allowing outer portion 190a to radially collapse for atraumatic removal of outer portion 190a from flow conduit 140. In an alternative embodiment, mandrel 190 can be configured with a varied geometry cross section, such as a circular or elliptical cross section within a major or minor axis that reduces along the length of device 100, or an elliptical cross section that changes to a circular cross section.

Figure 13A:
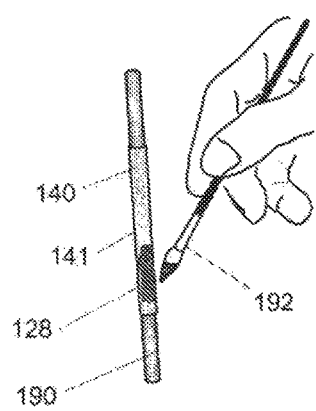
FIGS. 13a and 13b illustrate a series of sequential material application steps used in the fabrication of a graft device, consistent with the present invention.
Figure 13B:
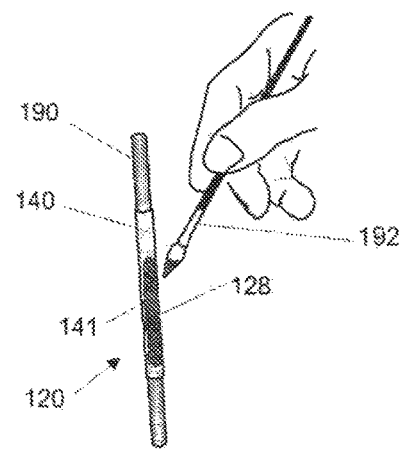

Referring now to FIGS. 13a and 13b, multiple views of a method for creating a graft device of the present invention are illustrated. FIG. 13a illustrates a side view of flow conduit 140 with outer wall 141 and inserted mandrel 190. Liquid covering material 128 is being applied to outer wall 141 with applicator tool 192 comprising a brush, roller or other tool adapted for applying a liquid to a surface. Liquid covering material 128 can include numerous liquid polymers, elastomers, or other liquid or suspension materials that are constructed and arranged for application of a biocompatible substance to a structure via an applicator tool subsequent to which material 128 hardens or otherwise solidifies. In a typical embodiment, liquid covering material 128 is selected from the group consisting of: a liquid silicone material, such as a silicone gel such as Sylgard; a hyrdrogel such as a fibrin get; gelatin; and combinations of these. Covering 120 has been formed from liquid material 128 during the application step of FIG. 13a. Additional application steps can be performed, including but not limited to: switching the end of mandrel 190 that is held during the application of liquid material 128; rotating mandrel 190; treating the flow conduit 140 with applied covering 120 such as treating with light, heat, air, a cross linking operation, and other exposures to cause liquid material 128 to solidify.

Figure 13C:
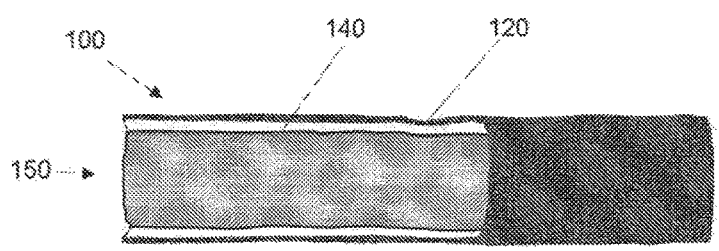
FIG. 13c illustrates a side partial sectional view of the graft device fabricated using the material application method of FIGS. 13a and 13b.

Referring additionally to FIG. 13c, covering 120 has a non-uniform surface comprising a varied thickness along the length of graft device 100. Graft device 100 includes lumen 150 within flow conduit 140, through which one or more solids, liquids and/or gases can flow.

Referring now to FIGS. 14 and 14a, a side sectional view and an exploded sectional view, respectively, of a graft device of the present invention are illustrated. Graft device 100, biased in a relatively linear bias as shown, includes lumen 150 from first end 101 to second end 102. Graft device 100 also includes flow conduit 340 which is surrounded on its outer wall or surface 141 by covering 120. Alternatively or additionally, covering 120 can surround the inner wall or surface 142 of flow conduit 140. Covering 320 can be a radially restrictive covering, such as a radially restrictive covering comprising a fiber matrix applied to flow conduit 140 during an electrospinning process. A restrictive covering can be used to limit radial expansion of flow conduit 140, such as when device 100 is used as a bypass graft in a cardiac bypass procedure. Covering 120 can be radially stretched prior to application around flow conduit 140, such as with a tube expanding device. Covering 120 can be radially shrunk after placement around flow conduit 140, such as when covering 120 is a material constructed and arranged to radially shrink with the application of heat light or a polymerization process. Flow conduit 140 can include any tissue or artificial structure, such as has been described hereabove, or can include both tissue and artificial materials.

As shown in FIG. 14*a*, an exploded view of graft device 100 at circle C1, covering 120 includes multiple channels 124 which have a curvilinear, tortuous geometry extending from the outer surface of covering 120 to the outer wall or surface 141 of flow conduit 140. Alternatively or additionally, numerous other configurations of channels can be included such as configurations selected from the group consisting of: relatively linear channels; channels that have at least one fluid connection point with another channel; channels that do not extend fully from the outer surface of covering 120 to the outer wall or surface 141 of flow conduit 140, channels that extend into a mid portion of How conduit 140, channels that extend to inner wall 142 of flow conduit 140; at least one channel 124 that extends from at least one of the inner surface 142 or the outer surface 141 of the flow conduit 140 where the channel 124 extends through at least a portion of a thickness of the covering 120; and combinations of these. Channels 124 can be created after application of covering 120 to flow conduit 140, during application of covering 120 to flow conduit 140 (e.g. during an electrospinning application of covering 120), or prior to application of covering 120 to flow conduit 140. Channels 124 can be created with one or more cutting or drilling tools, such as lasers, mechanical penetrators, chemical etchants, and the like. Channels 124 can be constructed and arranged to induce angiogenesis, to mimic the vasa vasorem of a vessel wall, or otherwise cause a physiologic response beneficial to the long term efficacy of an implanted device 100. Channels typically have a diameter between about 100 and about 200 microns, and a length range from about 100 to about 1000 microns.

Channels 124 can be positioned, sized and oriented using numerous techniques including the placement of hollow tubes which surround the channel, and the use of solid filaments which dissolve or are otherwise removed leaving channels in their place. In a particular embodiment, channels 124 include hollow tubes with straight, bent, or tortuous geometries, and with various sizes and lengths. The tubes can be made from materials that are resistant to the solvent that is used to prepare the polymer solution for creating covering 120. In one particular embodiment, the tubes are constructed from a salt based material that can be leached away after covering 120 is applied to flow conduit 140. After the tubes are leached away, channels 124 remain. Channels 124 can be included in flow conduit 140 prior to the application of covering 120 (e.g., via electrospinning, spraying, dipping, brushing, etc.) by applying these miniature tubes onto the surface of flow conduit 140, such as by applying with adhesive to maintain attachment and/or orientation. Channels 124 can be arranged in a random pattern or can include some preferential orientations (e.g., radial). After the covering 120 is deposited around flow conduit 140, previously covered with the miniature tubes, the resulting deposited external layer, covering 120, will be a composite of two materials. The first material is the deposited material, acting like the resin in a composite material. The second material is the miniature tubes, channels 124, acting like the fibers in a composite material. Covering 120 now includes many independent internal channels (as many as the number of little tubes). If the size and chemistry of these channels are supportive of cells adhesion and migration (e.g. some cytokines or growth factor internal treatment that performs as a chemo-attractant), channels 124 can sprout blood vessels coming from the surrounding tissues toward flow conduit 140. If channels 124 are radially oriented, the path required to cross the covering 120 by new capillary formation is minimized. The miniature tubes can be configured to dissolve or biodegrade over time, or can remain in place for at least a portion of the implant life of device 100.

Alternatively or additionally, leachable or fast degrading miniature filament-type rods (e.g. salt based rods) can be applied to flow conduit 140 prior to application of covering 120. These rods instead of acting as funnels per sc. dissolve (e.g., salt leaching) and leave channels 124 in covering 120 in a geometry similar to the space previously occupied by the rods.

In an alternative embodiment, channels in covering 120 or another portion of graft device 100 are eliminated or reduced, such as through the application of an adhesive or a relatively non-porous material, or compression or melting of areas surrounding the channels.

Figure 15A:
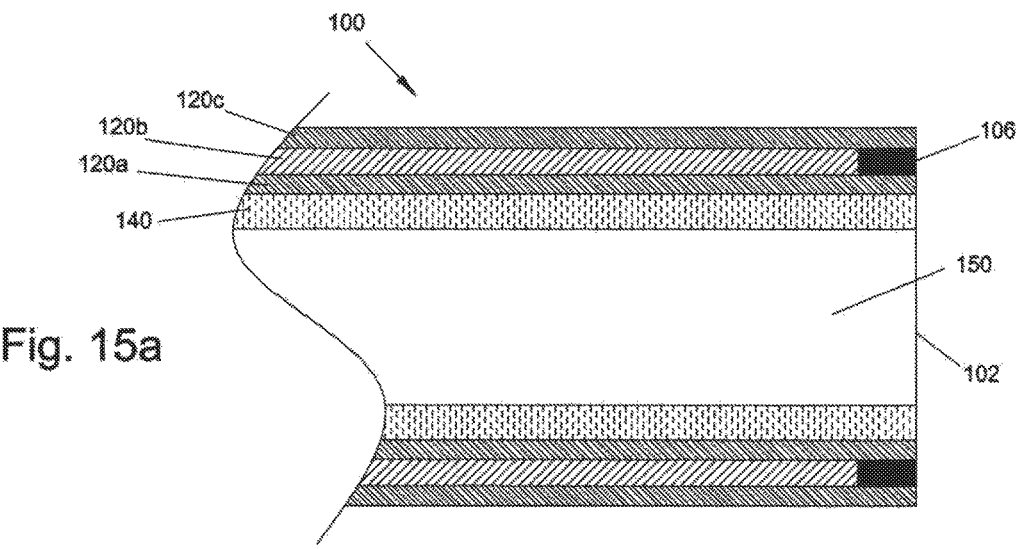
FIG. 15a illustrates a side sectional view of a graft device including a three layer covering, consistent with the present invention.
Figure 15B:
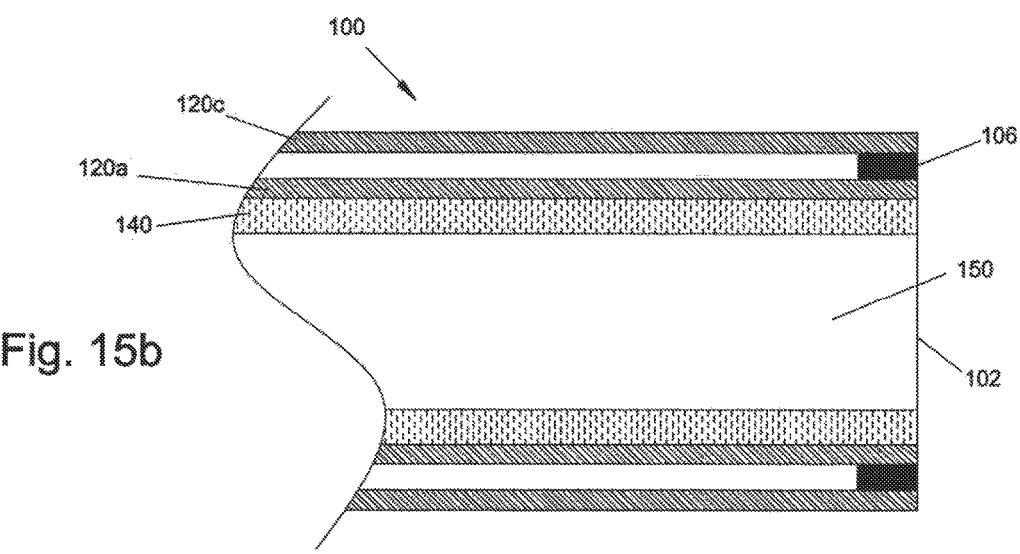
FIG. 15b illustrates a side sectional view of the graft device of FIG. 15a after one layer of the covering has biodegraded. consistent with the present invention.

Referring now to FIG. 15*a*, a side sectional view and an end portion of a graft device of the present invention is illustrated. Graft device 100, biased in a relatively linear bias as shown, includes lumen 150 within flow conduit 140 and extending to end 102. Flow conduit 140 includes a three-layer covering comprising first layer 120*a*, second layer 120*b* and third layer 120*e*. First layer 120*a* and third layer 120*c* are circumferentially attached at each device end (end 102 shown), by adhesive 106, typically a fibrin or elastomeric glue. As shown in FIG. 15*b*, second layer 120*b* is constructed and arranged to dissolve, biodegrade, or otherwise no longer be present when first layer 120*a* and third layer 120*c* are still intact. Second layer 120*b* can provide a transport barrier between first layer 120*a* and third layer 120*c* for a limited period of time. Second layer 120*b* can release chemoattractants to one or more of: flow conduit 140, lumen 150, first layer 120*a*, third layer 120*c*, or a (issue location exterior to device 100. After second layer 120*b* is partially or felly removed, first layer 120*a* and/or third layer 120*c* can extend into the space previously occupied by second layer 120*b*, such as when at least a portion of flow conduit 140 extends radially out, or at least a portion of third layer 120*c* extends radially in. Removal of second layer 120*b* can cause the radial resistance of device 100 to modify over time. In an alternative or additional embodiment, either or both first layer 120*a* and third layer 120*c* can be configured to biodegrade over time, such as both first layer 120*a* and third layer 120*c* biodegrading at similar or dissimilar rates.

Figure 16:
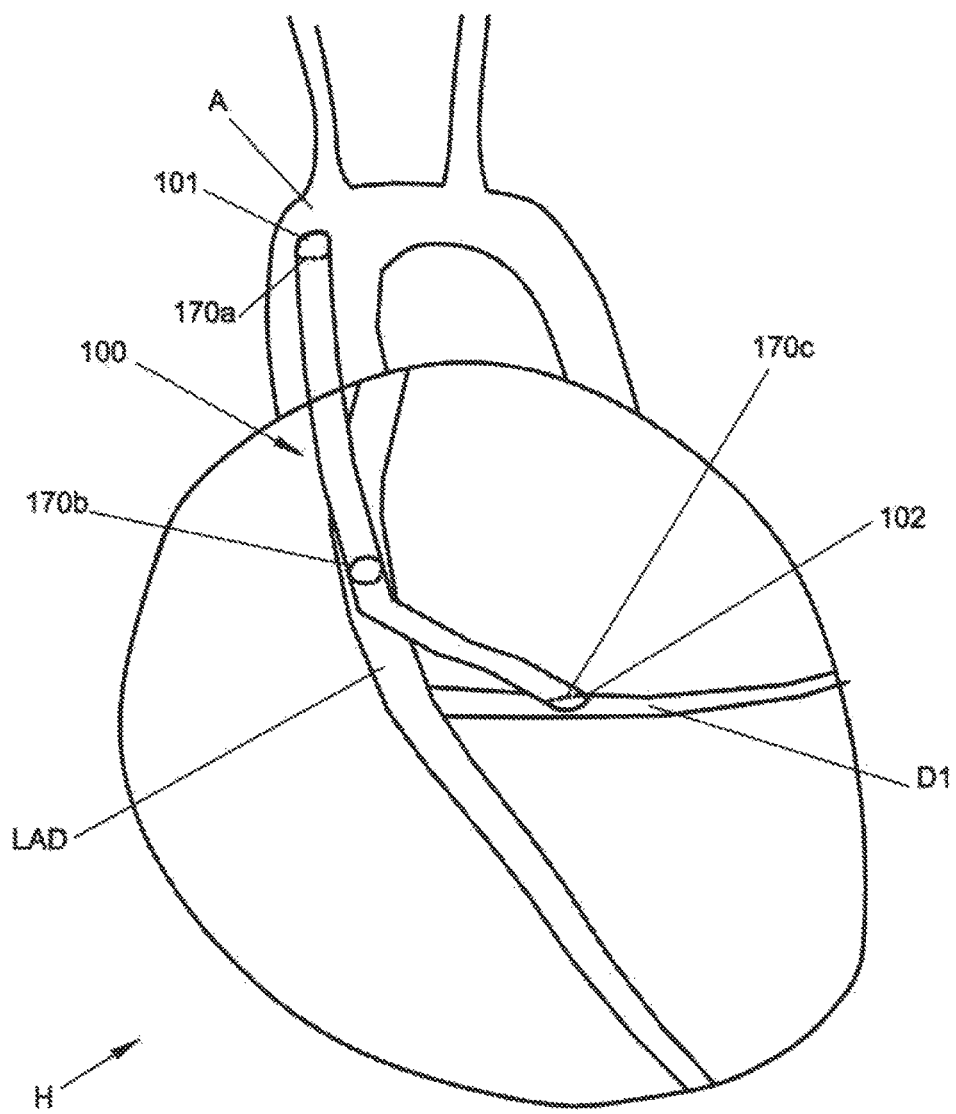
FIG. 16 illustrates a side view of a heart and aorta of a mammalian patient with a graft device attached to multiple vessels in a serial connection scheme, consistent with the present invention.

Referring now to FIG. 16, a side view of a heart and aorta of a mammalian patient with a graft of the current invention attached to multiple vessels in a serial connection scheme is illustrated. Graft device 100 includes first end 101 and second end 102. First end 101 is fluidly attached to the Aorta at connection 170*a*, an end to side anastomosis. A mid portion of graft device 100 is fluidly attached to the left anterior descending artery (LAD) at connection 170b, a side to side anastomosis. Second end 102 is fluidly attached to a diagonal of the LAD, D1, at connection 170c, another end to side anastomosis. Device 100 is serially attached to the patient's Heart such that blood flows from the Aorta into the LAD at connection 170b, and into D1 at connection 170c. An advantage of the serial connection scheme shown in FIG. 16 is that the flow through the portion of device 100 between connection 170a and 170b is increased due to the additional flow into connection 170c. Higher flow has been shown to improve patency of vein grafts in patients in numerous clinical studies. In one embodiment, graft device 100 comprises a covering surrounding a vessel graft, such as a harvested saphenous vein graft. The serial connection 170b is made at a location along the vein graft that previously included the ostium to or from a side branch of a harvested artery or vein. In other words, the opening in the side of the vein graft becomes the anastomotic site, yielding improved flow conditions. Device 100's covering is created such as to keep the side branch site intact. A hole punch or other tool can be used to make the corresponding opening in the covering. Numerous combinations of anastomosis and serial connections with one or more devices 100, such as a first device connected in an end to side anastomosis to a second device, can be used to achieve a desired flow configuration.

The curvilinear geometry of device 100 of FIG. 16 can be predetermined based on intended anastomotic connection sites, such as during an open surgical procedure or prior to that in a patient imaging procedure as has been described in detail hereabove. Device 100 can have had a curved mandrel inserted into the vessel graft prior 10 application of the covering, such as to bias device 100 in the shown geometry.

Figure 17A:
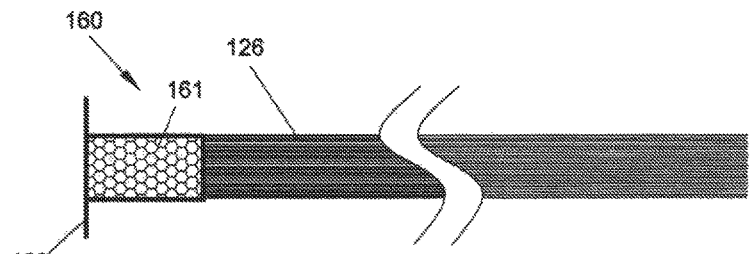
FIG. 17a illustrates a side view of an anastomotic connector including multiple Fibers extending from an end, consistent with the present invention.
Figure 17B:
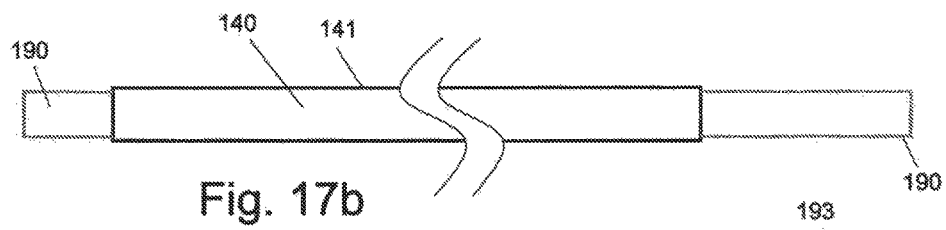
FIG. 17b illustrates a side view of a flow conduit, consistent with the present invention.
Figure 17C:
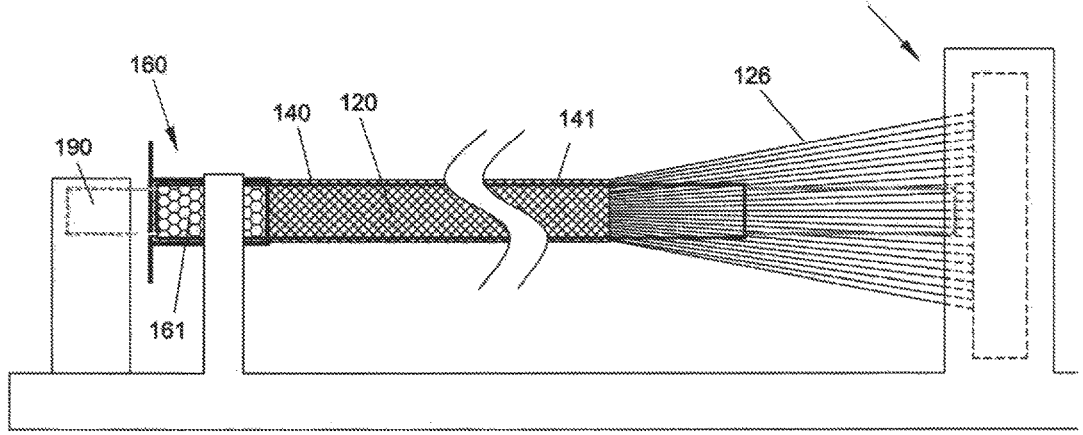
FIG. 17c illustrates a method of fabricating a graft device, including a device for weaving the fibers of the anastomotic connector of FIG. 17a around the flow conduit of FIG. 17b, consistent with the present invention.

Referring now to FIGS. 17a through 17c, multiple views of a method for creating a graft device of the present invention are illustrated. FIG. 17a illustrates a side view of anastomotic connector 160 which includes frame 161, flange 162, and multiple attached fibers 126 of the present invention extending from frame 161. FIG. 17b illustrates a side view of flow conduit 140 inserted over mandrel 190 and including outer wall 141. FIG. 17c illustrates a side view of an instrument creating a graft device of the present invention including anastomotic connector 160 of FIG. 17a and (low conduit 140 of FIG. 17b. Flow conduit 140 has been inserted within frame 161 of connector 160. Mandrel 190 has been removably coupled at each end to braiding instrument 193. Fibers 126 have been attached to braiding instrument 193, such that operation of braiding instrument 193 causes fibers 126 to be woven about or otherwise wrapped around outer wall 141 of flow conduit 140. In a particular embodiment, portions of fibers 126 are affixed to outer wall 141 or another portion of fiber 126 such as to prevent unwrapping of fibers 126. Fibers 126 can be fixed with one or more mechanisms such as a mechanism selected from the group consisting of: melted fibers such as fibers melted with the application of energy such as heat or application of a solvent; fibers fixed with an adhesive such as fibrin glue; fibers fixed with one or more knots or other frictionally engaging arrangements; and combinations of these.

Figure 18A:
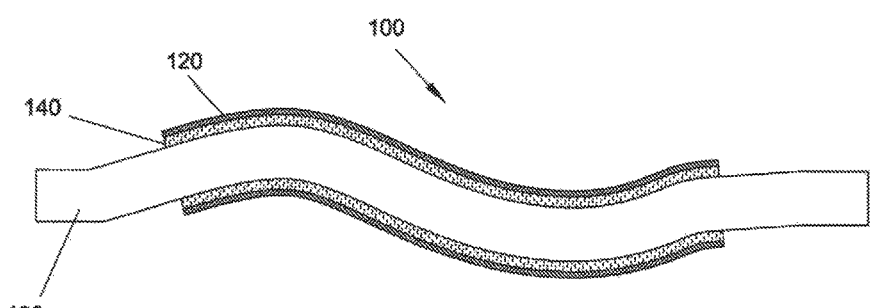
FIG. 18a illustrates a side sectional view of a non-linear mandrel surrounded by a graft device, consistent with the present invention.

Referring now to FIG. 18a, a side sectional view of a graft device of the present invention with a curvilinear configuration is illustrated. Graft device 100 is inserted over curvilinear mandrel 190 and includes flow conduit 140 and surrounding covering 120. The curvilinear configuration of mandrel 190 and graft device 100 can be based on patient anatomy, such as the anatomy proximate the aorta and one or more occluded arteries to be bypassed. The curvilinear configuration can be based on a visual or other analysis performed in an open surgical procedure, or a visualization procedure performed prior to surgery, such as an image created with a visualization apparatus as has been described in detail hereabove. Mandrel 190 can be malleable or otherwise shapeable, such that the mandrel can be shaped during the surgical procedure in the sterile setting. Mandrel 190 can be configured to transition between flexible and rigid configurations, such as a mandrel selected from the group consisting of: mandrels including gallium which can be made rigid at exposure to 30° C. and below; mandrels including shaped memory alloys or polymers configured to change from flexible to rigid on demand; liquid crystals that are configured to stiffen with the application of current; and combinations of these. In a particular embodiment, mandrel 190 is used in an electrospinning process to apply covering 120 and mandrel 190 includes electrically conductive material used in the electromagnetic field generation of the electrospinning process. In an alternative embodiment, a vasoconstrictor can be used to constrict flow conduit 140 around mandrel 190.

Figure 18B:
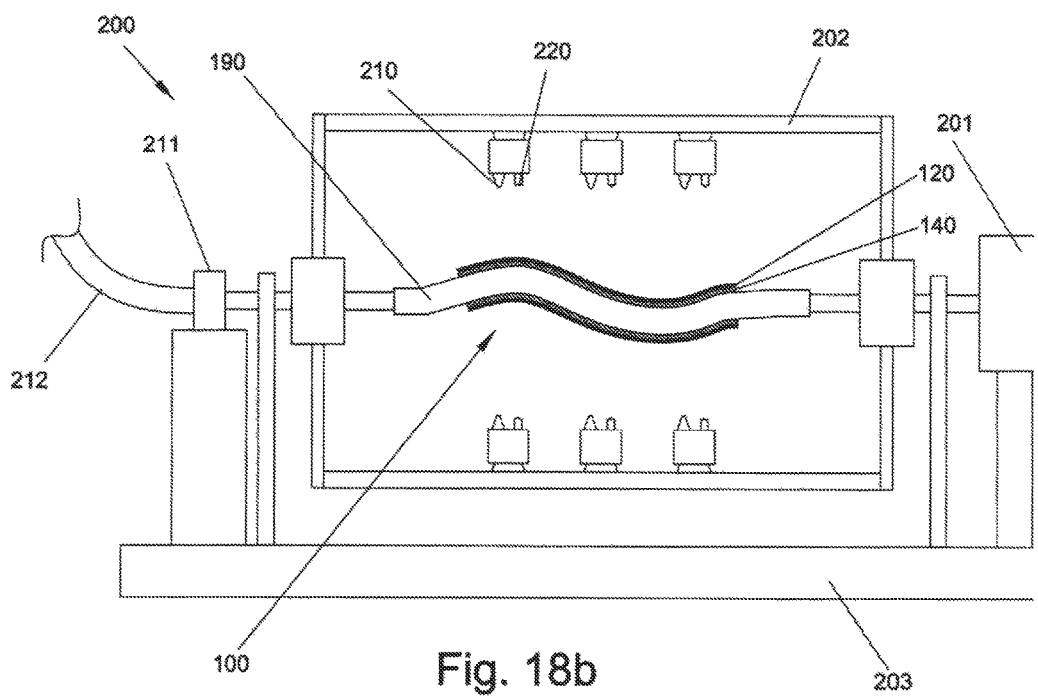
FIG. 18b illustrates a side view of an electrospinning instrument with the non-linear mandrel and graft device of FIG. 18a, consistent with the present invention.

Referring additionally to FIG. 18b, a side view of an electrospinning instrument with inserted nonlinear mandrel and graft device of FIG. 18a, all of the present invention, is illustrated. Electrospinning unit 200 is rotatably or fixedly attached to mandrel 190 which is surrounded by flow conduit 140. Electrospinning unit includes base 203 upon which motor 201 is fixedly mounted. Rotating frame 202 is rotatably mounted to base 203 such that nozzles 210 and lasers 220 can rotate about mandrel 190, such as with rotation of rotating frame 202 via motor 201, rotation of mandrel 190 via motor 201, or both. Conduit 212 is configured to supply energy and/or one or more electrospinning materials, such as electrical or laser energy to lasers 220 and/or polymer and/or other solutions to nozzles 210. Rotating connector 211 allows rotation of frame 202 and/or mandrel 190 while maintaining fluid scaled attachment to conduit 212. The configuration of electrospinning instrument 200 allows both straight and curved mandrels 190 to be inserted therein. Lasers 220 can be used during the electrospinning process to remove and/or modify portions of electrospun fibers. Lasers 220 can also be used to modify flow conduit 140, such as prior to beginning of electrospinning, or modify covering 120 after the electrospinning process has completed. Additionally or alternatively, lasers 220 can be used to mark flow conduit 140, indicating the direction of venous flow when flow conduit 140 is for example, a saphenous vein. Numerous other configurations of electrospinning instrument 190 or other fiber application instruments can be used to apply fibers to a flow conduit without departing from the spirit and scope of this application.

While the graft device of the present invention has mainly been described for connections between two vessels, such as the aorta and a coronary artery, numerous other body locations can be used for transporting gases, liquids or solids from a first body location to a second body location. While the flow conduit of the present invention has been mainly described as a harvested vessel such as a saphenous vein graft, numerous other tubular and other luminal structures can be used.

While the preferred embodiments of the devices and methods have been described in reference to the environment in which they were developed, they are merely illustrative of the principles of the inventions. Modification or combinations of the above-described assemblies, other embodiments, configurations, and methods for carrying out the invention, and variations of aspects of the invention that are obvious to those of skill in the art are intended to be within the scope of the claims. In addition, where this application has listed the steps of a method or procedure in a specific order, it can be possible, or even expedient in certain circumstances, to change the order in which some steps are performed, and it is intended that the particular steps of the method or procedure claim set forth herebelow not be construed as being order-specific unless such order specificity is expressly stated in the claim.

We claim:

1. A graft device for a patient, comprising:
   a tubular flow conduit comprising an inner wall, an outer wall, a proximal end, a distal end, and a lumen therethrough; and
   a tubular covering, said tubular covering surrounding a length of the tubular flow conduit and having an elastically biased curvilinear geometry customized for an anatomical geometry of an area of said patient;
   wherein said tubular covering is configured to impart an elastic curvilinear bias to the graft device, and
   wherein the graft device is constructed and arranged for connection between a first body space and a second body space.

2. The graft device of claim 1, wherein the graft device comprises a varying geometry cross section from the proximal end to the distal end of the tubular flow conduit.

3. The graft device of claim 1, wherein said anatomical geometry of an area of said patient is determined from an image produced by an instrument selected from the group consisting of: X-ray; MRI; Ct-Scan; NMR; Ultrasound; CCD Camera; film camera; and any combinations thereof.

4. The graft device of claim 1, wherein the tubular flow conduit comprises a tissue structure.

5. The graft device of claim 4, wherein the tissue structure is selected from the group consisting of: bone; skin; eustachian tube; artery; vein; urethra; lymphatic duct; nasal channel; intestine; esophagus; ureter; urethra; trachea; bronchi; duct; fallopian tube; and combinations thereof.

6. The graft device of claim 4, wherein the tissue structure is selected from the group consisting of: autologous tissue; allogenic tissue; xenogenic tissue; and combinations thereof.

7. The graft device of claim 4, wherein the tissue structure comprises a hollow tissue structure.

8. The graft device of claim 7, wherein the hollow tissue structure is selected from the group consisting of: eustachian tube; artery; vein; urethra; intestine; esophagus; ureter; urethra; trachea; fallopian tube; and combinations thereof.

9. The graft device of claim 4, wherein the tissue structure comprises a blood vessel.

10. The graft device of claim 4, wherein the tissue structure comprises cultured tissue.

11. The graft device of claim 10, wherein the cultured tissue is tissue grown proximate a tubular scaffold.

12. The graft device of claim 10, wherein the cultured tissue is tissue grown on a relatively flat plate.

13. The graft device of claim 10, wherein the cultured tissue is tissue grown in situ.

14. The graft device of claim 1, wherein the tubular flow conduit comprises an artificial conduit.

15. The graft device of claim 14, wherein the artificial conduit comprises material selected from the group consisting of: PFFE; ePTFE; PVDF-HFP; silicone; and combinations thereof.

16. The graft device of claim 1, wherein the tubular flow conduit comprises an artificial conduit and a tissue.

17. The graft device of claim 1, wherein the tubular covering comprises a polymer.

18. The graft device of claim 17, wherein the tubular covering comprises an electrospun polymer.

19. The graft device of claim 1, wherein the tubular covering comprises a fiber form.

20. The graft device of claim 19, wherein the fiber form comprises an electrospun fiber.

21. The graft device of claim 19, wherein the fiber form comprises a spooled fiber.

22. The graft device of claim 1, wherein the tubular covering is constructed and arranged to resist radial expansion of the tubular flow conduit.

23. The graft device of claim 1, wherein the tubular covering comprises an elongated tube constructed and arranged to slidingly receive the tubular flow conduit.

24. The graft device of claim 23, wherein the tubular covering is constructed and arranged to be shrunk after placement around the tubular flow conduit.

25. The graft device of claim 1, wherein the tubular covering comprises a helical coil constructed and arranged to surround the tubular flow conduit.

26. The graft device of claim 23, wherein the tubular covering is constructed and arranged to be expanded prior to slidingly receiving the tubular flow conduit.

27. The graft device of claim 1, wherein the tubular covering is constructed and arranged to support an anastomotic connection.

28. The graft device of claim 1, wherein the tubular covering comprises a slit tube constructed and arranged to surround the tubular flow conduit.

* * * * *